United States Patent
Danopoulos

(10) Patent No.: US 12,311,328 B2
(45) Date of Patent: May 27, 2025

(54) METHODS AND SYSTEMS FOR PHARMACEUTICAL COMPOUNDING

(71) Applicant: MEDISCA PHARMACEUTIQUE Inc., Quebec (CA)

(72) Inventor: Panagiota Danopoulos, Montreal (CA)

(73) Assignee: MEDISCA PHARMACEUTIQUE INC., Saint-Laurent (CA)

( * ) Notice: Subject to any disclaimer, the term of this patent is extended or adjusted under 35 U.S.C. 154(b) by 793 days.

(21) Appl. No.: 17/412,036

(22) Filed: Aug. 25, 2021

(65) Prior Publication Data

US 2022/0040654 A1 Feb. 10, 2022

Related U.S. Application Data

(63) Continuation of application No. 17/115,369, filed on Dec. 8, 2020, now Pat. No. 11,130,106, which is a
(Continued)

(51) Int. Cl.
*B01F 35/00* (2022.01)
*B01F 29/10* (2022.01)
(Continued)

(52) U.S. Cl.
CPC .......... *B01F 35/2209* (2022.01); *B01F 29/10* (2022.01); *B01F 29/34* (2022.01);
(Continued)

(58) Field of Classification Search
CPC .......... B01F 35/2209; B01F 35/221422; B01F 29/10; B01F 35/2117; B01F 35/22161;
(Continued)

(56) References Cited

U.S. PATENT DOCUMENTS

| 5,352,037 A | 10/1994 | Jouvin |
| 8,226,291 B2 | 7/2012 | Zamirowski et al. |

(Continued)

FOREIGN PATENT DOCUMENTS

| DE | 10066151 B4 | 10/2010 |
| DE | 102010060650 A1 | 5/2011 |

(Continued)

OTHER PUBLICATIONS

Friedrich WO 2017036597 (Year: 2017).*
(Continued)

*Primary Examiner* — Anshu Bhatia
(74) *Attorney, Agent, or Firm* — Finnegan, Henderson, Farabow, Garrett & Dunner LLP

(57) ABSTRACT

A computer-implemented method for execution by a processor of a computing device. The method comprises implementing a computerized graphical user interface (GUI) that provides a user of the computing device with an opportunity to identify a pharmaceutical compounding formula; consulting a database at least partly on a basis of the identified pharmaceutical compounding formula in order to determine mixing parameters for a planetary mixer, associated with the identified pharmaceutical compounding formula; and causing a mixer to subject a container to superimposed rotation and revolution movements in accordance with the mixing parameters determined from consulting the database.

12 Claims, 34 Drawing Sheets

Related U.S. Application Data continuation of application No. PCT/CA2019/050799, filed on Jun. 7, 2019.

(60) Provisional application No. 62/750,453, filed on Oct. 25, 2018, provisional application No. 62/686,984, filed on Jun. 19, 2018.

(51) Int. Cl.
  *B01F 29/34* (2022.01)
  *B01F 35/21* (2022.01)
  *B01F 35/22* (2022.01)
  *B01F 35/221* (2022.01)
  *G16C 20/90* (2019.01)
  *B01F 101/22* (2022.01)

(52) U.S. Cl.
  CPC ...... *B01F 35/2117* (2022.01); *B01F 35/2205* (2022.01); *B01F 35/2207* (2022.01); *B01F 35/221422* (2022.01); *B01F 35/22161* (2022.01); *G16C 20/90* (2019.02); *B01F 35/2206* (2022.01); *B01F 2101/22* (2022.01)

(58) Field of Classification Search
  CPC .. B01F 29/34; B01F 35/2207; B01F 35/2205; B01F 35/2206; B01F 2101/22; G16C 20/90
  See application file for complete search history.

(56) References Cited

U.S. PATENT DOCUMENTS

| | | | |
|---|---|---|---|
| 8,932,417 | B1 | 1/2015 | Renz et al. |
| 10,231,903 | B2 | 3/2019 | Danopoulos et al. |
| 10,239,063 | B2 | 3/2019 | Vester et al. |
| 10,352,671 | B1 | 7/2019 | Freeman et al. |
| 10,420,705 | B2 | 9/2019 | Danopoulos et al. |
| 10,765,600 | B2 | 9/2020 | Danopoulos et al. |
| 11,130,106 | B2 | 9/2021 | Danopoulos et al. |
| 2005/0086008 | A1* | 4/2005 | DiGianfilippo ......... G07F 13/06 702/19 |
| 2010/0161113 | A1 | 6/2010 | Tribble et al. |
| 2010/0185322 | A1 | 7/2010 | Bylsma et al. |
| 2015/0036450 | A1* | 2/2015 | Vester .................... B01F 31/70 366/108 |
| 2016/0045876 | A1 | 2/2016 | Kaucky et al. |
| 2018/0125753 | A1 | 5/2018 | Danopoulos |
| 2019/0224073 | A1 | 7/2019 | Danopoulos et al. |
| 2020/0345581 | A1 | 11/2020 | Danopoulos et al. |
| 2020/0345582 | A1 | 11/2020 | Danopoulos et al. |
| 2021/0086150 | A1 | 3/2021 | Danopoulos et al. |

FOREIGN PATENT DOCUMENTS

| | | |
|---|---|---|
| WO | 2014083029 A2 | 6/2014 |
| WO | 2014144814 A1 | 9/2014 |

OTHER PUBLICATIONS

Extended Search Report (communicated Jul. 1, 2024) dated Jun. 17, 2024, issued in EP Patent Application No. 24167610.5 (10 pages).
Examination Report No. 2 for Standard Patent Application, dated Jul. 2, 2024, issued by the Australian Government IP Australia (4 pages).

* cited by examiner

310

| | Account # | Username | Password | Other Info |
|---|---|---|---|---|
| | 312A | 312U | 312P | 312O |
| 310A → | 001 | | | |
| 310B → | 002 | | | |
| 310C → | 003 | | | |
| 310D → | 004 | | | |
| 310E → | 005 | | | |
| | ... | ... | ... | ... |

| | SOP # | Mixer Make/Model | Functionality | Formulation Property | File |
|---|---|---|---|---|---|
| | 352A | 352M | 352F | 352P | 352D |
| 350A → | A | | | | |
| 350B → | B | | | | |
| 350C → | C | | | | |
| 350D → | D | | | | |
| 350E → | E | | | | |
| | ... | ... | ... | ... | ... |

FIG. 3B

Mixer Functionality: Mixing Cream/Gel Topicals

Formulation Property: HRT Cream Containing 10% or Less of Active Ingredients

Process Steps:

1) Weigh active powders directly in mixer
2) Add wetting agent on top of powders (optional)
3) Record gross weight of mixing container and preparation
4) Set counter-balance
5) Mix at X rpm for Y minutes
6) Add base on top of levigated powder
7) Record gross weight of mixing container and preparation
8) Set counter-balance
9) Mix and Z rpm for Y seconds

FIG. 3E

Mixer Functionality: Reduce Particle Size of Powders

Formulation Property: Crystalized and Large Particle Powders

Steps:

1) Weigh active powders directly in stainless steel mixing container
2) incorporate milling media
3) record gross weight of mixing container and preparation
4) Set counter-balance
5) Mix at X rpm for Y seconds
6) Take mixer container out and shake vigorously to prevent clumping
7) Mix again at Z rpm for W seconds
8) Remove beads by pouring micronized powder and beads over a large mm sieve or strainer
9) Add wetting agent
10) Mix at X rpm for Y seconds
11) Add base to levigated powder
12) Record gross weight of mixing container and preparation
13) Set counter balance
14) Mix at X rpm for W seconds

FIG. 3F

| Formula | Total Weight | Operating Parameters |
|---|---|---|
| ABC | 1-100g | 45 seconds @ 2000 rpm |
| | 101-500g | 1 minute @ 2500 rpm |
| XYZ | 1-500g | 1 minute @ 2000 rpm |
| | 501-1000g | 2 minutes @ 1800 rpm |
| ... | ... | ... |

1210

FIG. 12

METHODS AND SYSTEMS FOR PHARMACEUTICAL COMPOUNDING

CROSS-REFERENCE TO RELATED APPLICATIONS

This application is a continuation application and claims priority under 35 U.S.C. § 120 to U.S. application Ser. No. 17/115,369, filed on Dec. 8, 2020, issued as U.S. Pat. No. 11,130,106, which is a continuation application of PCT Application No. PCT/CA2019/050799, filed on Jun. 7, 2019, which claims the benefit under 35 U.S.C. 119(e) of U.S. Patent Application Ser. No. 62/686,984, filed on Jun. 19, 2018 and of U.S. Patent Application Ser. No. 62/750,453, filed on Oct. 25, 2018, which are all incorporated by reference herein in their entireties.

FIELD

The present disclosure relates to pharmaceutical compounding and, in particular, to improved methods and systems for pharmaceutical compounding using planetary mixers.

BACKGROUND

Planetary mixers are specialized machines used in homogenizing and degassing liquids such as paints, dyes and adhesives. They are also used for mixing and micronizing powders. Planetary mixers use a combination of rotation and revolution of a container to achieve a high degree of performance (homogenizing, degassing, micronizing, etc.) in a short amount of operating time.

Recently, the pharmaceutical compounding industry has taken note of planetary mixers. However, due to the relative dearth of experience in the area, novice users can waste a significant amount of time and product in search of operating parameters that yield satisfactory results. Also, problems may arise due to human error being introduced into the mixing process.

As such, improvements are needed in the area of pharmaceutical compounding using planetary mixers.

SUMMARY

According to a first aspect, there is provided a computer-implemented method for execution by a processor of a computing device, comprising:
  implementing a computerized graphical user interface (GUI) that provides a user of the computing device with an opportunity to specify a pharmaceutical compounding formula;
  consulting a database at least partly on a basis of the specified pharmaceutical compounding formula in order to determine mixing parameters for a planetary mixer, the mixing parameters being associated with the specified pharmaceutical compounding formula in the database; and
  causing a motor assembly to apply superimposed rotation and revolution movements to a container in accordance with the mixing parameters determined from said consulting step.

According to another aspect, there is provided a computing device, comprising: at least one processor; and a non-transitory storage medium operably connected to the at least one processor and storing computer-readable program instructions. The at least one processor is configured to execute the program instructions, wherein execution of the program instructions by the at least one processor causes carrying out of a method that comprises:
  implementing a computerized graphical user interface (GUI) that provides a user of the computing device with an opportunity to specify a pharmaceutical compounding formula;
  consulting a database at least partly on a basis of the specified pharmaceutical compounding formula in order to determine mixing parameters for a planetary mixer, the mixing parameters being associated with the specified pharmaceutical compounding formula in the database; and causing a motor assembly to apply superimposed rotation and revolution movements to a container in accordance with the mixing parameters determined from said consulting.

According to another aspect, there is provided a non-transitory medium storing computer-readable instructions which, when read and executed by at least one processor of a computing device, cause the device to carry out a method that comprises:
  implementing a computerized graphical user interface (GUI) that provides a user of the computing device with an opportunity to specify a pharmaceutical compounding formula;
  consulting a database at least partly on a basis of the specified pharmaceutical compounding formula in order to determine mixing parameters for a planetary mixer, the mixing parameters being associated with the specified pharmaceutical compounding formula in the database; and
  causing a motor assembly to apply superimposed rotation and revolution movements to a container in accordance with the mixing parameters determined from said consulting.

According to another aspect, there is provided a system, comprising a digital storage medium storing computer-readable instructions; a database of SOP files for producing pharmaceutical formulations using a mixer, each of the SOP files being associated in the database with a mixer functionality and a formulation property; and a processor coupled to the digital storage medium and to the database, and configured to execute the computer-readable instructions in the digital storage medium. According to this aspect, execution of the computer-readable instructions causes the processor to implement a graphical user interface and to carry out a method that comprises:
  prompting a user to enter, via the graphical user interface, a selection of a mixer functionality from a set of mixer functionality options presented by the graphical user interface;
  prompting a user to enter, via the graphical user interface, a selection of a formulation property from a set of formulation property options presented by the graphical user interface;
  identifying in the database one of the SOP files, based on the selected mixer functionality and the selected formulation property; and
  sending a message conveying the identified SOP file to an external device via a communication interface.

According to another aspect, there is provided a communication device for control of a planetary mixer, comprising at least one processor and a non-transitory storage medium operably connected to the at least one processor and storing computer-readable program instructions. The at least one processor being configured to execute the program instructions, wherein execution of the program instructions by the at least one processor causes instantiation of a mixer control application that is configured for:

receiving input from a user of the communication device via a graphical user interface implemented by the computer-readable instructions;

communicating with a remote database over the internet to provide the remote database with the input from the user and to obtain from the remote database an SOP file in response thereto, the SOP file specifying operating parameters for operating a planetary mixer to produce a pharmaceutical formulation;

encoding the operating parameters into control messages for the planetary mixer; and communicating the control messages to the planetary mixer to control operation of the mixer in accordance with the operating parameters.

According to another aspect, there is provided a computing device, comprising at least one processor; and a non-transitory storage medium operably connected to the at least one processor and storing computer-readable program instructions. The at least one processor being configured to execute the program instructions. According to this aspect, execution of the program instructions by the at least one processor causes carrying out of a method that comprises:

receiving input from a user of the communication device via a graphical user interface implemented by the computer-readable instructions;

communicating with a remote database over the internet to provide the remote database with the input from the user and to obtain from the remote database an SOP file in response thereto, the SOP file specifying operating parameters for operating a planetary mixer to produce a pharmaceutical formulation;

encoding the operating parameters into control messages for the planetary mixer; and communicating the control messages to the planetary mixer to control operation of the mixer in accordance with the operating parameters.

According to another aspect, there is provided a non-transitory medium storing computer-readable instructions which, when read and executed by at least one processor of a computing device, cause the device to carry out a method that comprises:

receiving input from a user of the communication device via a graphical user interface implemented by the computer-readable instructions;

communicating with a remote database over the internet to provide the remote database with the input from the user and to obtain from the remote database an SOP file in response thereto, the SOP file specifying operating parameters for operating a planetary mixer to produce a pharmaceutical formulation;

encoding the operating parameters into control messages for the planetary mixer; and communicating the control messages to the planetary mixer to control operation of the mixer in accordance with the operating parameters.

According to another aspect, there is provided a computer-implemented method for compounding using a planetary mixer, comprising obtaining a computer-readable SOP file associated specifying a procedure for compounding a pharmaceutical formulation using a planetary mixer, the SOP file specifying at least: a suggested first mixing step, a suggested second mixing step, and a step intermediate the suggested first and second mixing steps requiring the container to be removed from the planetary mixer;

monitoring a lid sensor of the planetary mixer to determine whether the planetary mixer is open or closed;

monitoring a motor assembly of the planetary mixer to determine that an actual first mixing step corresponding to the suggested first mixing step has been completed; and disabling further mixing by the motor assembly until the monitoring determines that the planetary mixer has been opened after completion of the actual first mixing step.

According to another aspect, there is provided a computer-implemented method comprising:

obtaining a computer-readable SOP file specifying a procedure and ingredients for compounding a pharmaceutical formulation using a planetary mixer;

acquiring identification data for a particular ingredient to be placed in a container to be mixed by the planetary mixer;

consulting a database containing identification data for the ingredients specified by the SOP file to compare the identification data for the particular ingredient against the identification data for the ingredients specified by the SOP file;

carrying out an action that depends on the comparing.

According to another aspect, there is provided a manufacturing method, comprising:

filling a container with a combination of ingredients corresponding to a pharmaceutical formula;

using a tag writer to write to an electronic tag on the container, thereby to cause the tag to store information regarding the combination of ingredients contained in the container;

at a tag reader, electronically reading the electronic tag of the container to extract the information regarding the combination of ingredients contained in the container; and using a mixer to mix the contents of each container according to a set of operating parameters that depend on the information extracted from the electronic tag.

According to another aspect, there is provided a planetary mixer, comprising:

a holder for a container;

a motor assembly configured to impart superimposed revolution and rotation movements to a container placed in the holder, in accordance with controllable operating parameters;

a tag reader configured to read a tag on a container to extract information about the contents of the container; and a processing device configured to determine operating parameters for the mixer based on the extracted information about the contents of the container and to control the superimposed revolution and rotation movements imparted to the container by the motor assembly in accordance with the determined operating parameters.

According to another aspect, there is provided a computer-implemented method, which comprises:

recording transmissions to an account holder of SOP files for producing pharmaceutical formulations using a mixer, each of the SOP files being associated in a storage medium with one or more ingredients;

recording ingredient purchases by the account holder;

identifying an anomalous ingredient supply condition for the account holder based on the recorded transmissions of SOP files and the recorded ingredient purchases;

signaling the anomalous ingredient supply condition to an external device via an interface.

The aforementioned method may further comprise estimating an expected ordering pattern from the recorded transmissions of SOP files, wherein the anomalous ingredient supply condition is identified based on the expected ordering pattern and the recorded ingredient purchases.

According to another aspect, there is provided a universal adapter and container assembly for planetary mixing, comprising:
- a container;
- an adapter for placement in the container, at least part of the adapter being made of a material that is malleable to espouse a contour of a subject container at rest and for which the subject container causes a surface deformation of no more than 1% at 800 RPM rotation and 2000 RPM revolution.

According to another aspect, there is provided a universal adapter and container assembly for planetary mixing, comprising:
- a container;
- an adapter for placement in the container, at least part of the adapter being made of a material that is selected so as to be sufficiently deformable, while the container is at rest, to espouse at least part of a contour of each of a plurality of differently configured subject containers;
- the material being further selected so as to have a hardness that is capable of being controllably increased.

Either of the aforementioned universal adapter may further comprise a first adapter portion configured to be placed towards a bottom of the container; and a second adapter portion configured to be placed on top of the subject container when the subject container is placed on top of the first adapter portion.

According to another aspect, there is provided a container assembly for planetary mixing, comprising:
- a container with a bottom, and a side wall defining a mouth, and a cover;
- a plurality of micronizing beads in the container;
- a filter cap, the filter cap being securable to the mouth of the container, the filter cap having a plurality of apertures, the apertures and the micronizing beads being dimensioned so as to prevent the micronizing beads from exiting the container.

In the aforementioned container, the cover and the mouth of the container may have complementary threads, and the filter cap and the mouth of the container may also have complementary threads.

In the aforementioned container, the filter cap may remain secured to the mouth of the container after removal of the cover.

According to another aspect, there is provided a container for mixing pharmaceutical compounds, comprising a read-writable electronic tag storing operating parameters for mixing the contents of the container using a planetary mixer.

In the aforementioned container, the read-writable tag may be an RFID tag.

In the aforementioned container, the read-writable electronic tag may further store information regarding ingredients of a pharmaceutical compound contained in the container.

BRIEF DESCRIPTION OF THE DRAWINGS

In the present disclosure, reference will be made to the accompanying drawings, in which:

FIG. 3A illustrates a credentials table for storing account information, in accordance with a non-limiting embodiment.

FIG. 3B illustrates an SOP table for storing operating procedure information, in accordance with a non-limiting embodiment.

FIGS. 3E and 3F are a non-limiting examples of an operating procedure, in accordance with a non-limiting embodiment.

FIG. 12 illustrates table for storing information about a variety of formulas, in accordance with a non-limiting embodiment.

The drawings are intended merely to assist in the understanding of certain embodiments, and should be considered non-limiting.

DETAILED DESCRIPTION

Figure 1:
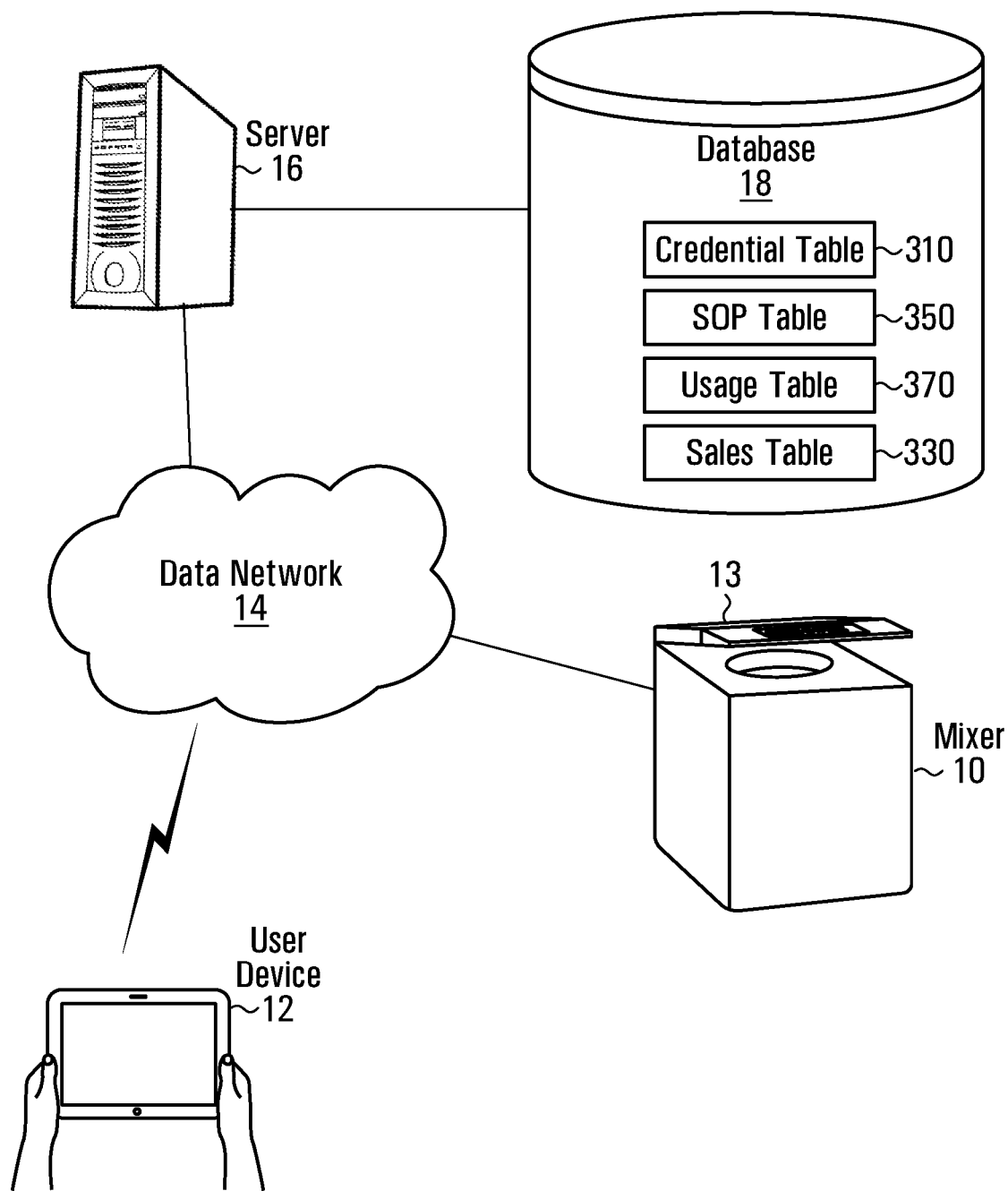
FIG. 1 is a block diagram showing a mixer environment, including a mixer and a system for communicating between a user device and a server over a data network, in accordance with a non-limiting embodiment.

With reference to FIG. 1, there is shown a mixer 10 with a lid 13, a user device 12, a data network 14, a server 16 and a database 18. In an embodiment, the mixer 10 can be a planetary mixer. The planetary mixer may have a variety of functions, such as to perform mixing and de-aeration simultaneously by concurrently revolving and rotating a mixing container. Other functions of the planetary mixer may include milling and melting.

In this first embodiment, the mixer 10 may, but need not, be communication-enabled or network-enabled. For example, in this first embodiment, the mixer 10 can be a stand-alone device, whereby to use the mixer 10, one places the products to be mixed into the mixing container, weighs the container, sets the counter-balance to the corresponding value, loads the container into the mixer 10, closes the lid 13, chooses one's settings, and pushes start. A suitable non-limiting example of a non-network-enabled mixer of this type may be any of the Maz™ mixer models KK-300SS, KK-400W and KK-1000W, sold by Medisca Pharmaceutique Inc. of St-Laurent, Canada.

The user device 12 is configured to communicate with the server 16 over the data network 14. In an embodiment, the user device 12 can be implemented as a mobile phone, a tablet, a desktop PC or a console, to name a few non-limiting possibilities. The user device 12 includes a memory, a processing entity (e.g., at least one processor), a screen and a network interface, amongst other standard components associated with the aforesaid implementations. The memory of the user device 12 may store computer-readable instructions that are executed by the processing entity of the user device 12 in order to cause the user device 12 to carry out certain processes.

In an embodiment, the data network 14 may be a public data network (such as the Internet) or a local area network. In an example of a non-limiting embodiment, the server 16 may be a World Wide Web server. In an embodiment, the database 18 may be part of a memory internal to the server 16 or may be external to the server 16 and connected thereto by a bus or over a data network (such as the internet).

Figure 2A:
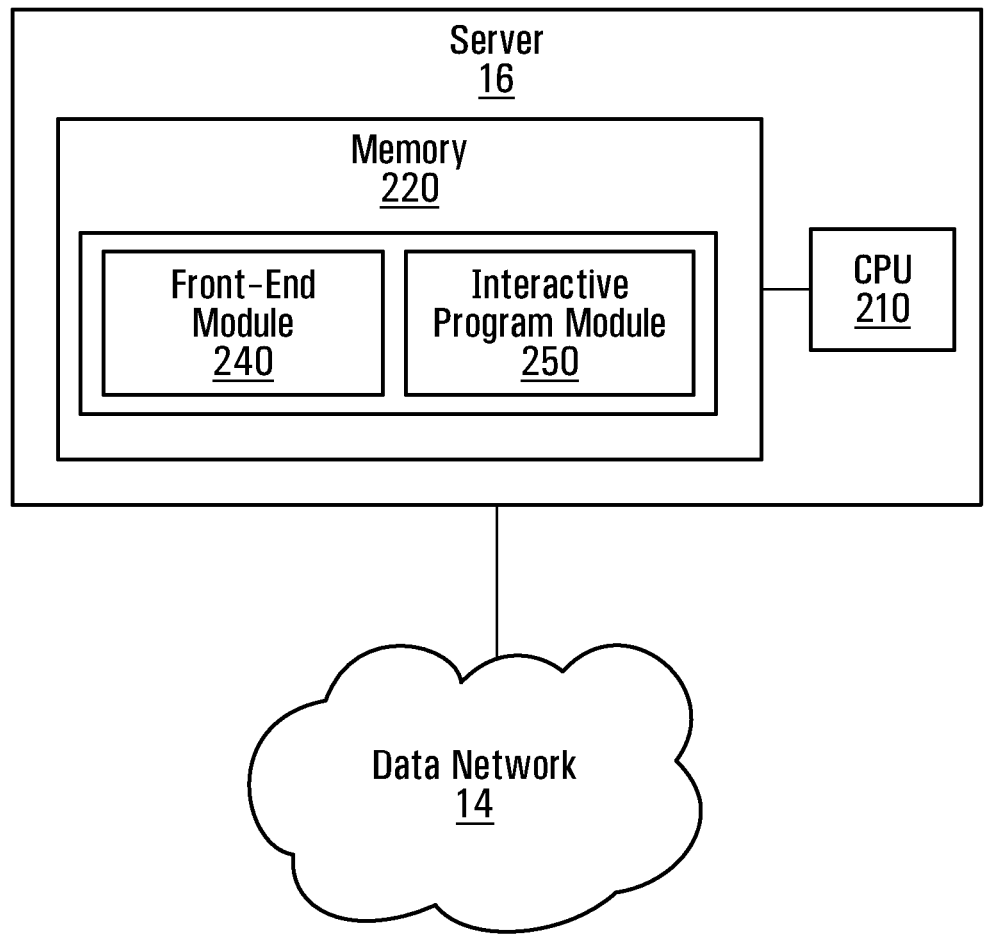
FIG. 2A is a block diagram showing components internal to the server, in accordance with a non-limiting embodiment.

With reference to FIG. 2A, the server 16 includes a processor (CPU) 210 and a memory 220 that stores computer-readable instructions executable by the processor 210. Execution of the computer-readable instructions by the processor 210 causes the server 16 to implement a front-end module 240 and an interactive program module 250 (which may also be referred to as a "bot" or "wizard"). In some arrangements, the server 16 may be managed by, or property of, a manufacturer or distributor of pharmaceutical compounding equipment and/or materials.

Figure 2B:
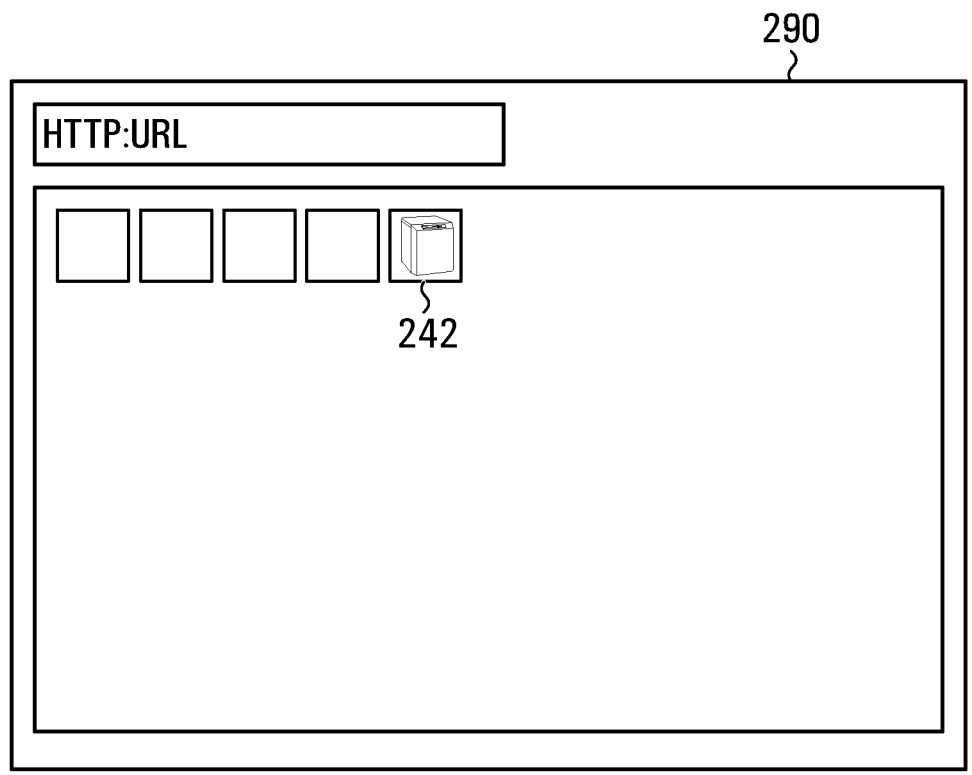
FIG. 2B shows a page for display on the user device during connection to the server, in accordance with a non-limiting embodiment.

The server 16 is accessible by the user device 12 via the data network 14. That is to say, a user of the user device 12 may enter into communication with the server 16 by specifying a particular URL corresponding to the server 16, or by activating a software application (app) associated with the server 16. With reference to FIG. 2B, in response to being contacted at the particular URL (or via the app), the server 16 is configured to execute the front-end module 240. The front-end module 240 may cause an activatable link or icon 242 corresponding to the interactive program module 250 to be presented on the screen of the user device 12. The front-end module 240 is configured to detect activation (e.g., clicking or selecting through the user device 12) of the link or icon 242 and, in response to such activation, may launch the interactive program module 250. Launching the interactive program module 250 may include executing computer-readable instructions which, when executed by the processor 210, cause the server 16 to present a graphical user interface 290 to the user device 12 over the data network 14.

Figure 3C:
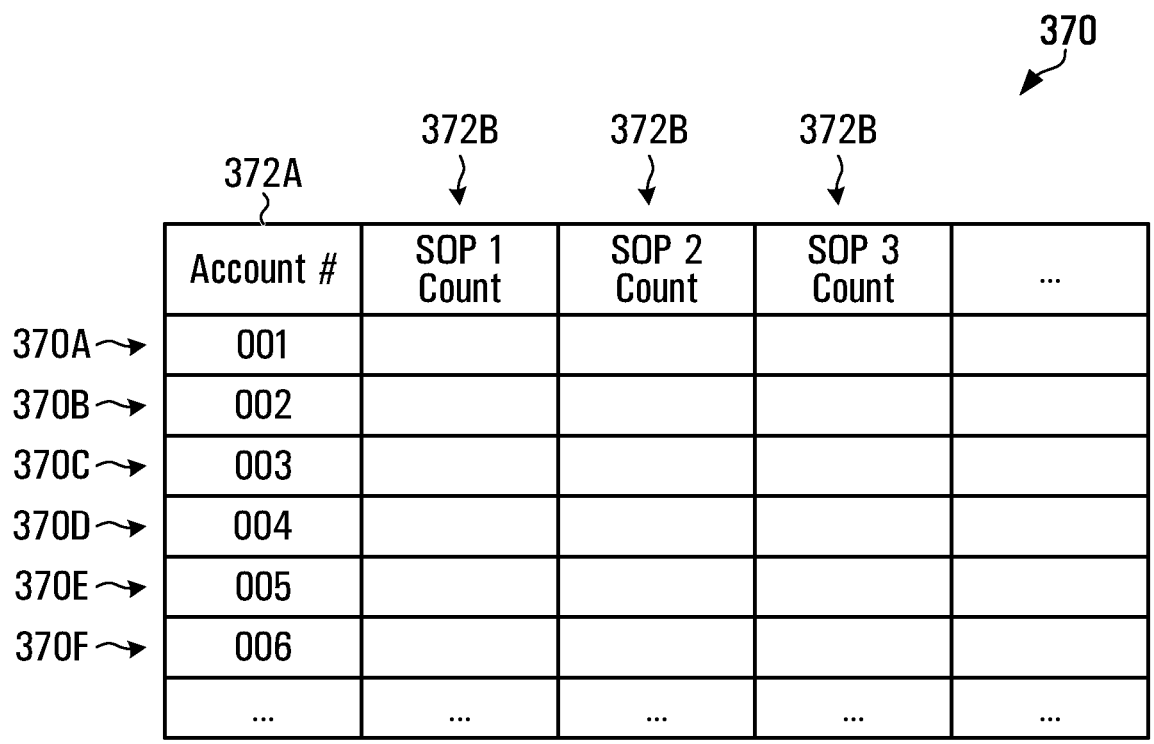
FIG. 3C illustrates a table for storing operating procedure information in association with account information, in accordance with a non-limiting embodiment.

In an embodiment, the front-end module 240 may perform an account verification process before allowing the link or icon 242 to be activated. To this end, reference is made to FIG. 3A, in which are shown possible contents of the database 18 conceptualized as a table 310 of records 310A . . . 310E, hereinafter referred to as a "credentials table". Each of the records 310A . . . 310E in the credentials table 310 includes a plurality of entries, in each of an account #field 312A, a username field 312U, a password field 312P and possibly other fields (e.g., other information field 312O). For a given one of the records 310A . . . 310E, the entry in the account #field 312A is information corresponding to a particular account holder associated with that record (e.g., it could be a unique account number or customer name or legal entity name). The entry in the username field 312U and password field 312P represents credential information that may be set up by the account holder during a prior "account setup" phase. The entry in the other info field 312O could be related to other information associated with the account holder, such as make and model of a mixer known to have been purchased by the account holder, the date of purchase, the software version and servicing information, to name a few non-limiting possibilities. Of course, those skilled in the art will appreciate that the reference to a "table" being used for account information is merely a conceptualization of an otherwise tangible and non-transitory medium for storing such information. In this regard, the database 18 may implement any suitable organizational format or data structure in lieu of the credentials table 310.

Returning now to FIGS. 2A and 2B, as part of the account verification process, the front-end module 240 may be configured to request credentials (e.g., a username and/or password) from the user device 12. The front-end module 240 verifies these credentials against the information stored in the credentials table 310 of the database 18 and requires a match before the interactive program module 250 is launched and presented to the user via the user device 12. Once the correct credentials corresponding to a particular account holder are entered, the front-end module 240 from now on assumes that all interactions with the user are on behalf of the rightful account holder.

In the present embodiment, according to one of its functionalities, the interactive program module 250 is configured to obtain and transmit an "SOP file" to a requesting user device, such as the user device 12. An SOP file can be a computer-readable digital or electronic file that encodes or specifies a particular "operating procedure" (sometimes referred to as a "standard operating procedure" or SOP), which may include an ordered set of process steps for operating the mixer 10 for a specified pharmaceutical compounding formula, i.e., so as to achieve a specific functionality for a specific formulation and using a specific make and model of planetary mixer.

The database 18 may be used for storing the information relevant to multiple operating procedures. In this regard, and with reference now to FIG. 3B, there is shown possible contents of the database 18, conceptualized as a table 350 of records 350A . . . 350E in memory, hereinafter referred to as an "SOP table". Each of the records 350A . . . 350E is associated with a respective operating procedure and includes a plurality of entries in a plurality of fields. The fields may include an SOP #field 352A, a mixer make/model field 352M, a functionality field 352F, a formulation property field 352P and a file field 352D. These fields are now described in further detail.

The SOP #field 352A for the record associated with a given operating procedure stores a unique identifier of the given operating procedure.

The "functionality" field 352F may specify information regarding a specific use of the mixer 10. Non-limiting examples of functionality are varied and can include one or more of (i) particle size reduction (micronization/grinding); (ii) melting; (iii) mixing of powders; (iv) mixing of creams/gels/topicals and (v) de-aerating (degassing).

The "formulation property" field 352P may specify information regarding the specific delivery form, dosage or other properties of the formulation that is to be produced by the mixer 10. Non-limiting examples of formulation property are varied, and in some cases it is not an independent choice but rather depends on the mixer functionality. In some embodiments, formulation properties are selectable and a set of selectable formulation properties may be different for at least two different mixer functionalities.

For example, in a non-limiting embodiment, one can have the following association between mixer functionality and formulation property:

| Mixer functionality: | Formulation property: |
|---|---|
| Particle size reduction | Lidocaine powder; Crystallized and large particle powders |
| Tablets | Enteric coated; Non-coated |
| Homogenizing powders | Progesterone capsules; Bi-estrogen capsules without progesterone; Bi-estrogen capsules with progesterone; Non-HRT powders |
| Mixing cream/gel/topical compounds | HRT Cream containing 5% or less active ingredients; HRT Cream containing more than 5% active ingredients |

Another example of the "mixer functionality" could be whether or not an adapter is to be used in the mixing process, such adapter being configured to hold the final dispensing container from which the prepared formulation is to be dispensed. This is in contrast to the situation where, once mixed in a mixing container, the mixed formulation is to be transferred from the mixing container into a dispensing container. As such, if the mixer functionality is selected to be "adapter mixing", there may be an implicit assumption that the intended use of the mixer is for mixing a cream/gel/topical compound in a dispensing container. This may lead to additional granularity (which can be referred to as a sub-functionality) when selecting the "adapter mixing" functionality. For example,

| Mixer functionality: | Mixer sub-functionality |
|---|---|
| Adapter mixing | Pump adapter |
| Adapter mixing | 15 ml-50 ml Unguator jar adapter |
| Adapter mixing | 100 ml Unguator jar adapter; |
| Adapter mixing | 100 ml Samix jar adapter |
| Adapter mixing | Universal adapter |

The "mixer make/model" field 352M for the record associated with a given operating procedure is optional and may identify the manufacturer, model and size of planetary mixer for which the given operating procedure has been designed. This is to accommodate differences in the calibration of RPM, counter-balance, mixing time and order of steps from one manufacturer, model or size of planetary mixer to another, even where the mixer functionality and the formulation properties remain the same.

Finally, the "file" field 352D for the record associated with a given operating procedure includes a name of, or a pointer to, an SOP file, namely a digital or electronic file that encodes or specifies the given operating procedure. The way in which an SOP file encodes or specifies a given operating procedure is not particularly limiting. By way of non-limiting example, the SOP file could be a text file that specifies the ordered set of process steps forming the given operating procedure.

As mentioned above, the operating procedure encoded or specified by an SOP file may include a sequence of ordered process steps. Some of these process steps for operating the mixer may involve the setting of "operating parameters" for controlling operation of the mixer 10. The operating parameters can in some cases be provided to the mixer 10 using an input/output interface of the mixer 10 (such as a screen display with key/button input).

Examples of operating parameters that may be specified in a given process step of a given operating procedure may include, without limitation, one or more of:
   rotation speed (in rpm),
   revolution speed (in rpm),
   time (in seconds); and
   counter-balance weight (in grams).

With reference to FIG. 3E, there is shown a generalized non-limiting example of contents of an SOP file for a first non-limiting operating procedure. In this example, the mixer functionality is "mixing cream/gel/topical compounds" and where the formulation property is "HRT Cream Containing 10% or Less of Active Ingredients". This first operating procedure includes 9 process steps. It is seen that process steps 4 and 5 involve mixing according to a first set of operating parameters and process steps 8 and 9 involve mixing according to a second set of operating parameters.

With reference to FIG. 3F, there is shown a generalized non-limiting example of contents of an SOP file for a second non-limiting operating procedure. In this example, the mixer functionality is "particle size reduction" and where the formulation property is "Crystalized and Large Particle Powders". This second operating procedure includes 14 process steps. It is seen that process steps 4 and 5 involve mixing according to a first set of operating parameters, process step 7 involves mixing according to a second set of operating parameters, process step 10 involves mixing according to a third set of operating parameters and process steps 13 and 14 involve mixing according to a fourth set of operating parameters.

In some embodiments, a single process step may involve multiple consecutive mixing stages, each with its own operating parameters, together with intervening pauses. As such, an example of operating parameters that may be specified in two mixing stages of a given process step of a given operating procedure may include:

| Process step 1 | Mixing stage 1 | Rotation @RT1 rpm |
| | | Revolution @RV1 rpm |
| | | Time T1 seconds |
| | | Counter-balance C1 grams |
| | Pause | P seconds |
| | Mixing stage 2 | Rotation @RT2 rpm |
| | | Revolution @RV2 rpm |
| | | Time T2 seconds |
| | | Counter-balance C2 grams |

In one embodiment, the operating parameters that may include revolution speeds of from at least 400 revolutions per minute ("rpm" or "RPM"). For example, a suitable revolution speed can be in the range of from 400 to about 4000 rpm, or from 400 to about 2000 rpm, or any suitable value within these ranges. In one embodiment, the operating parameters may include revolution:rotation rpm ratios of about 10:4.

In certain embodiments, the revolution rpm, the rotation rpm and the mixing time are configurable parameters and their values may be individually selectable. Alternatively, they may be selectable from pre-determined combinations of parameter values that are provided at the time of designing the operating procedure and creating its SOP file. In other embodiments, the ratio between rotation rpm and revolution rpm may be a configurable parameter and thus would constrain the revolution rpm for a certain rotation rpm or vice versa. Moreover, the geometric configuration of the mixer 10 (e.g., the eccentricity (distance between the center of rotation and the center of revolution), the dimensions of the container, etc.), combined with the revolution rpm and rotation rpm, results in a certain acceleration (G-force, measured in g or $m/s^2$) being felt by the material in the container. In some embodiments, the desired G-force may be an operating parameter input to the mixer 10, which could then result in selection, by the mixer 10, of a suitable revolution rpm and/or rotation rpm.

As such, the desired G-force could be an operating parameter that forms part of one of a given one of the process steps of a given one of the SOP files stored in the database 18. For example, the minimum or maximum G-force may be specified as an operating parameter, resulting in thresholding of the rotation rpm and/or the revolution rpm, depending on the values entered. In still further embodiments, certain operating parameters (such as the rotation rpm or the revolution rpm) may be dynamic (i.e., vary over time) and may be encoded in the SOP file as a function of time so as to define a pre-determined curve. There may exist still further controllable operating parameters of superimposed revolution and rotation movements implemented by the mixer 10, such as the total weight of the container being mixed.

Of course, those skilled in the art will appreciate that the reference to a "table" being used for storing records (including links/pointers to SOP files) is merely a conceptualization of an otherwise tangible and non-transitory medium for storing such information. In this regard, the database 18 may implement any suitable organizational format or data structure in lieu of the SOP table 350.

Figure 4A:
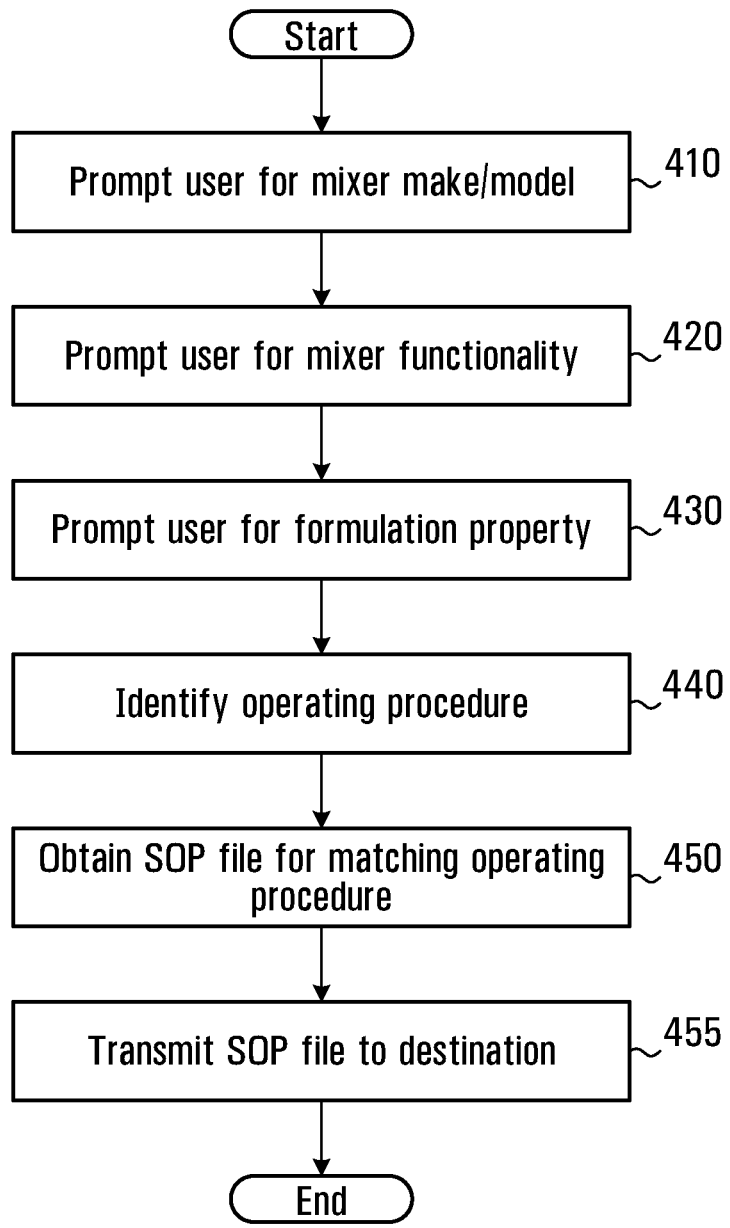
FIG. 4A is flowchart illustrating steps that may be taken by an interactive program module in order to retrieve an operating procedure based on user input, in accordance with a non-limiting embodiment.
Figure 4B:
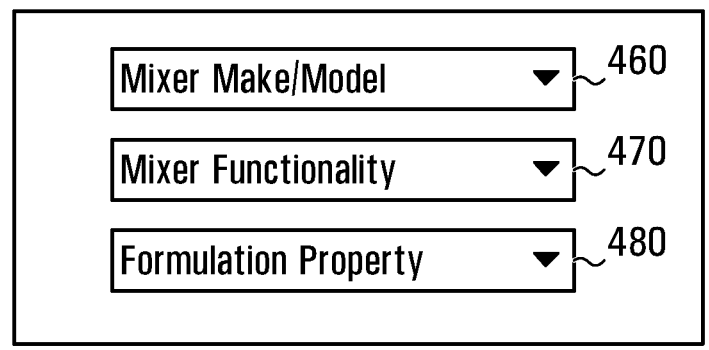
FIG. 4B illustrates a graphical user interface (GUI) on the user device that may appear during execution of the flowchart in FIG. 4A, in accordance with a non-limiting embodiment.

Reference is now made to FIG. 4A, which shows a flowchart illustrative of a series of steps that may be executed by the interactive program module 250 once it is launched. It is recalled that the interactive program module 250 interacts with the user through a graphical user interface (GUI) 290 presented via the user device 12, as illustrated in FIG. 4B. The user is assumed to be the rightful account holder of a particular user account, as described above.

At step 410, the interactive program module 250 causes the GUI 290 to display a graphical element 460 (e.g., a dialog box or menu) that presents a set of mixer make and model options, from which the user is prompted to make a selection. The set of mixer make and model options may be the set of all mixer make and model options for the various records stored in the SOP table 350.

At step 420, the interactive program module 250 causes the GUI 400 to display a graphical element 470 (e.g., a dialog box, list or graphical menu) that presents a set of mixer functionality options, from which the user is prompted to make a selection. The set of mixer functionality options may be the set of all mixer functionality options for the various records stored in the SOP table 350, or it may be limited to only those associated with records that have matching mixer make and model as selected at step 460.

At step 430, the interactive program module 250 causes the GUI 290 to display a graphical element 480 (e.g., a dialog box, list or graphical menu) that presents a set of formulation properties, from which the user is prompted to make a selection. It should be noted that the set of formulation properties presented via the GUI 290 may depend on the selected mixer functionality option. In other words, different selections of the functionality option will lead to different available selections of the formulation properties.

In this way, the user can specify a pharmaceutical compounding formula (e.g., a specified list of ingredients and their relative quantities by weight, volume or concentration) with inputs through the GUI 290, which can include the mixer and model option, the mixer functionality option, and the formulation property option but is not limited thereto.

At this point in the process, the interactive program module 250 will have received various selections from the user and may have enough information to identify and obtain an SOP file. This is attempted at step 440. In particular, the interactive program module 250 consults the SOP table 350 in order to identify an appropriate one of the records 350A . . . 350E that matches the user selections. Then, at step 450, the corresponding SOP file for the identified record is retrieved from memory, e.g., via the filename or pointer stored in the file field 352D for the identified record.

At step 455, the SOP file is transmitted to a destination associated with the account holder. In an embodiment, the SOP file can be sent to the user device 12 over the data network 14 and the GUI 290; in another embodiment, the SOP file can be sent to an email address associated with the account holder, which could be stored in the other info field 3120 of the credentials table 310. Encryption or password protection can be used to keep the contents of the email secure.

It should be appreciated that some steps may be performed in a different order than what is illustrated in FIG. 4A.

In an embodiment, the interactive program module 250 may be configured to track the frequency with which the SOP files are consulted or retrieved by each account holder. Accordingly, reference is made to FIG. 3C, where there is shown a table 370 of records 370A . . . 370F, hereinafter referred to as a "usage table". Each of the records 370A . . . 3F0D includes a plurality of entries, in each of an account #field 372A and a plurality of SOP count fields 372B. For a given one of the records 370A . . . 370F, the entry in the account #field 372A is information corresponding to a particular account holder associated with that record, as previously described (e.g., it could be a unique account number or customer name or legal entity name). As for the SOP count fields 372B, each of these fields may pertain to a different SOP file that was requested by the account holder in question. Of course, those skilled in the art will appreciate that the reference to a table is merely a conceptualization, as other organizational formats or data structures may be suitable and may thus be employed instead of a table. It will be appreciated that the usage table 370 may further store the times at which the various SOP files were requested by the various account holders.

Figure 3D:
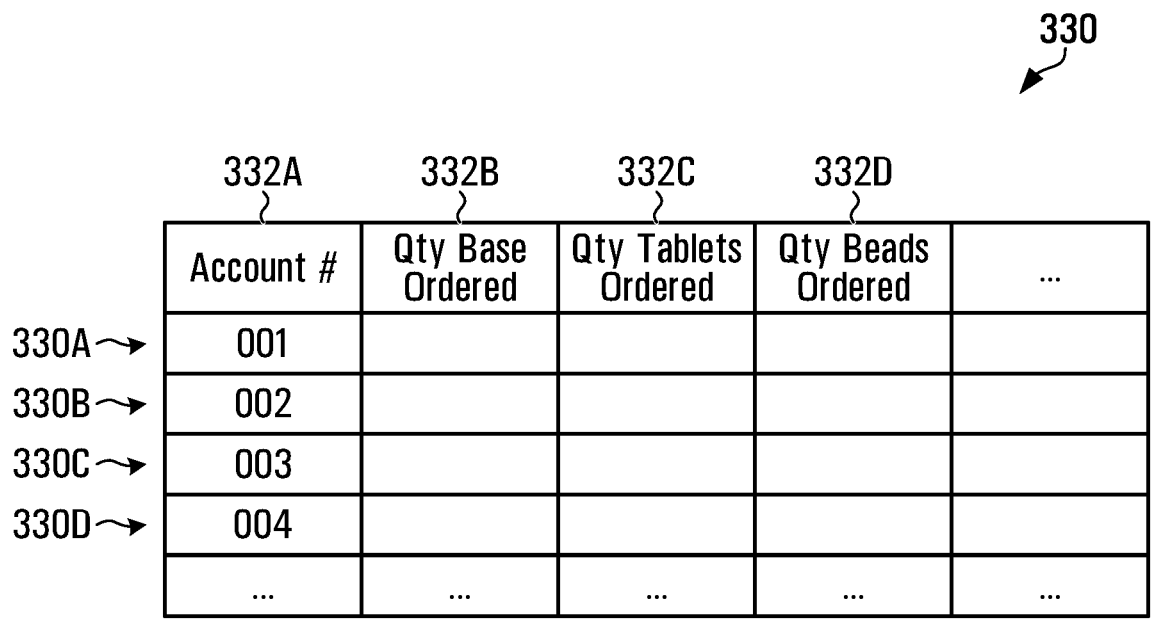
FIG. 3D illustrates a table for storing ingredient and quantity information in association with account information, in accordance with a non-limiting embodiment.
Figure 3G:
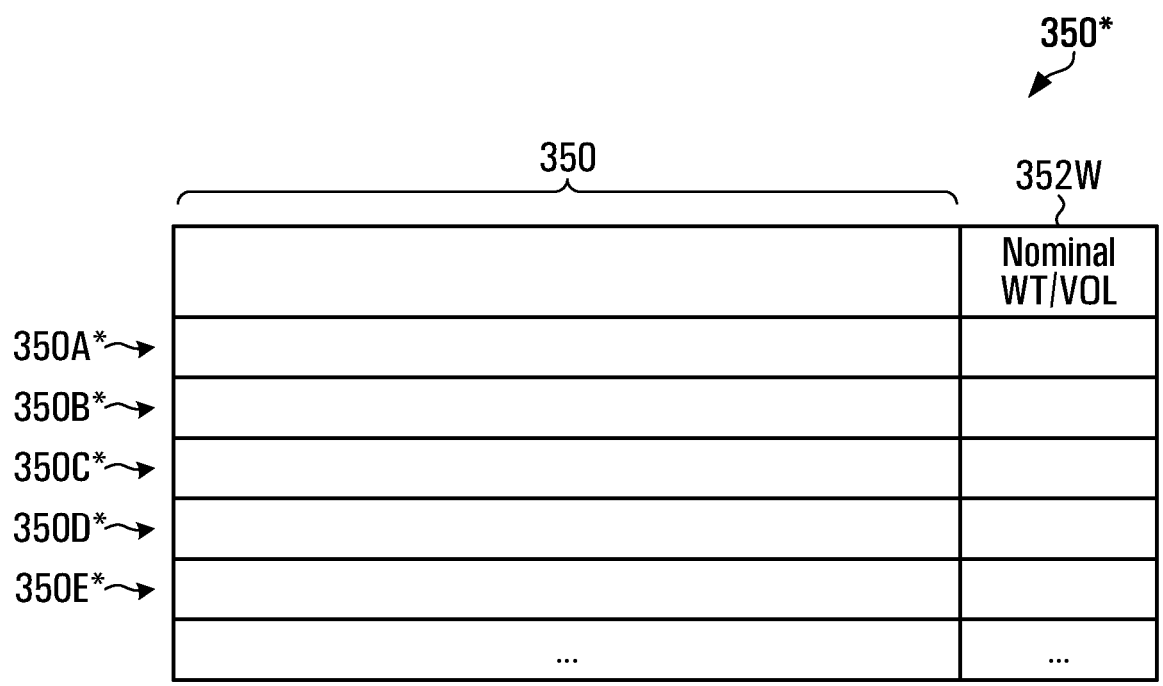
FIG. 3G illustrates a variant of the table in FIG. 3B, including an additional field, in accordance with a non-limiting embodiment.

It should also be appreciated that some operating procedures may require certain quantities of ingredients to be used in order to achieve a particular overall weight or volume of formulation (or range of weights/volumes). As such, some operating procedures may be further associated with a nominal weight/volume. To this end, FIG. 3G shows an SOP table 350*, is a variant of SOP table 350. SOP table 350* includes a plurality of records 350A* . . . 350E*. In SOP table 350*, each of the records 350A* . . . 350E* includes the same fields as SOP table 350, namely an SOP #field 352A, a mixer make/model field 352M, a functionality field 352F, a formulation property field 352P and a file field 352D. In addition, each of the records 350A* . . . 350E* in SOP table 350* includes a nominal weight/volume field 352W, which indicates the weight or volume of formulation that the respective operating procedure is specifically tailored for. As such, there may be multiple records associated with operating procedures for which the only difference is the entry in the nominal weight/volume field.

Figure 3H:
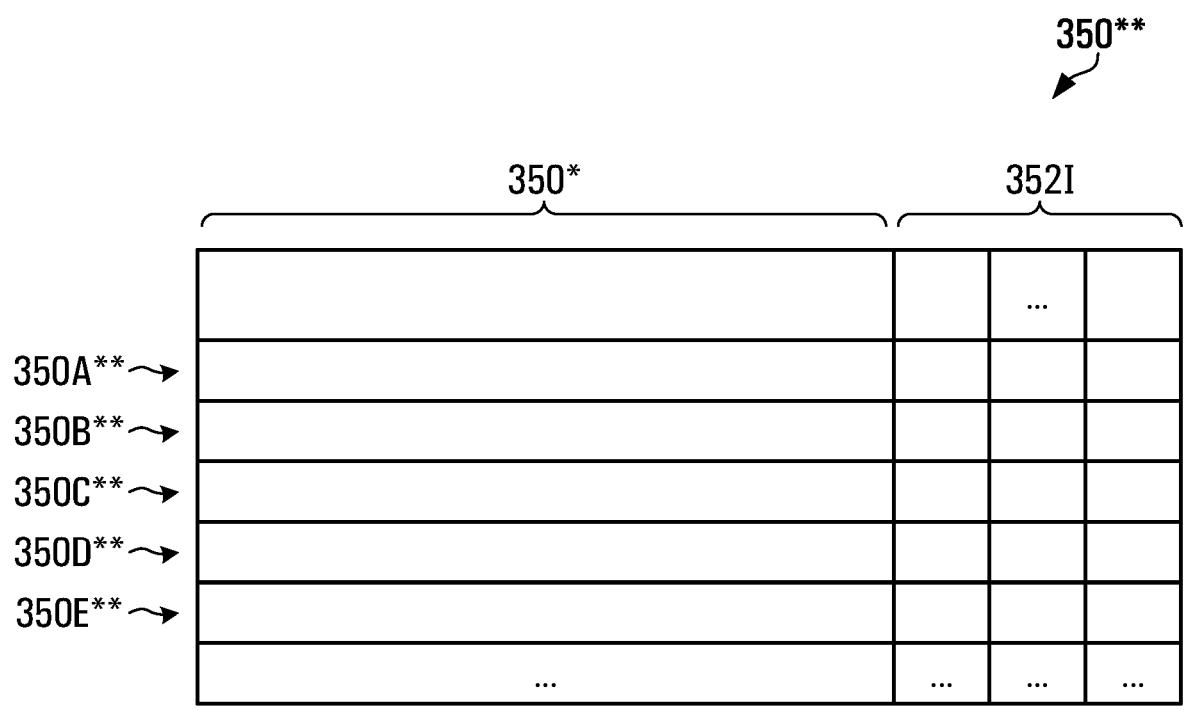
FIG. 3H illustrates a variant of FIG. 3G including additional fields, in accordance with a non-limiting embodiment.

In a variant, shown in FIG. 3H, an SOP table 350 includes records 350A . . . 350E**, each of which includes the same fields as the records in SOP table 350* of FIG. 3G. Additionally, one or more fields 352I is provided, which indicate specific quantities of ingredients associated with each associated operating procedure. These ingredients may be categorized at a coarse level (e.g., cream, base, oil, flavor, capsule, etc.) or they may be specified at a granular level (e.g., progesterone, size 0 EEZIFIT, size 00 CONISNAP #40, etc.). As increasing numbers of specialized operating procedures are developed for increasingly sophisticated versions of the interactive program module 250, it is expected that more and more granularity will be associated with the ingredients associated with each operating procedure (and stored in fields 352I of SOP table 350**).

Figure 5A:
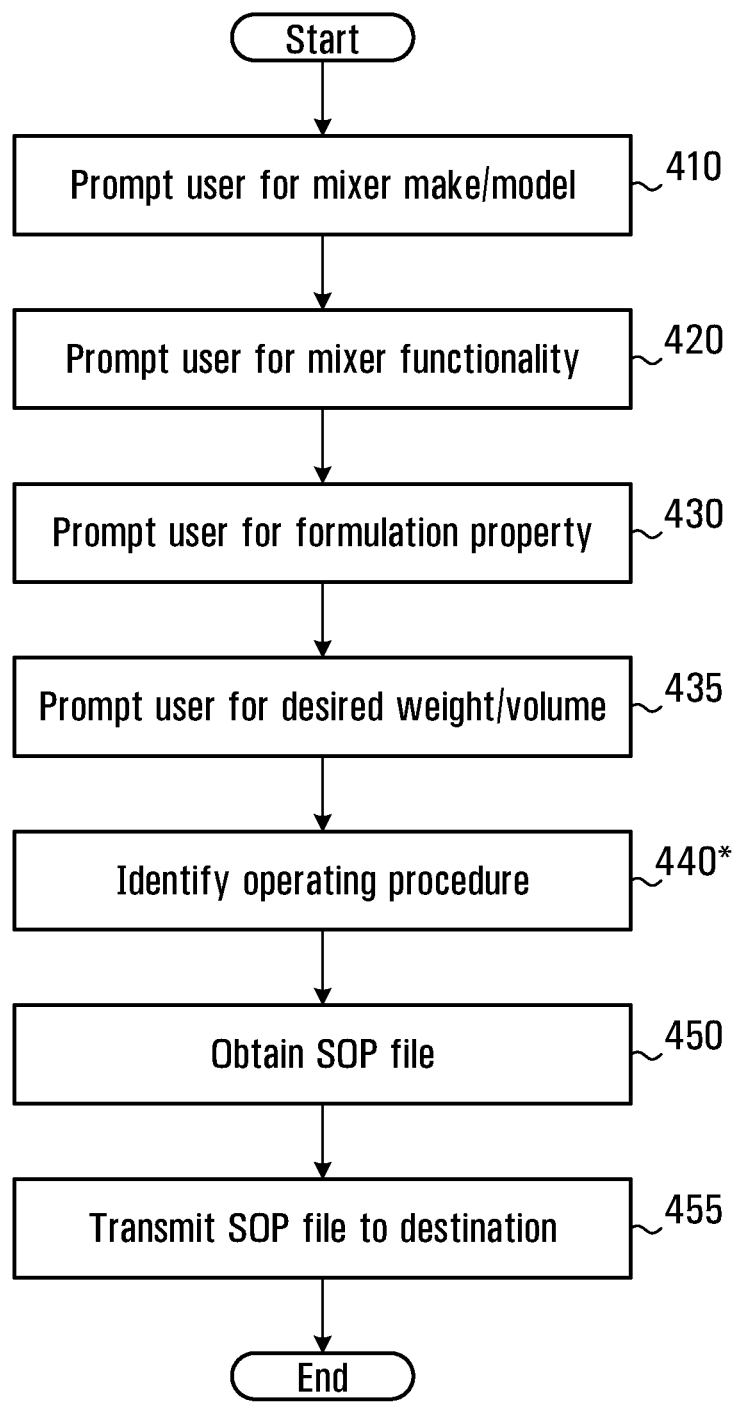
FIG. 5A is a variant of FIG. 4A with an additional step to obtain a desired weight or volume from the user, in accordance with a non-limiting embodiment.
Figure 5B:
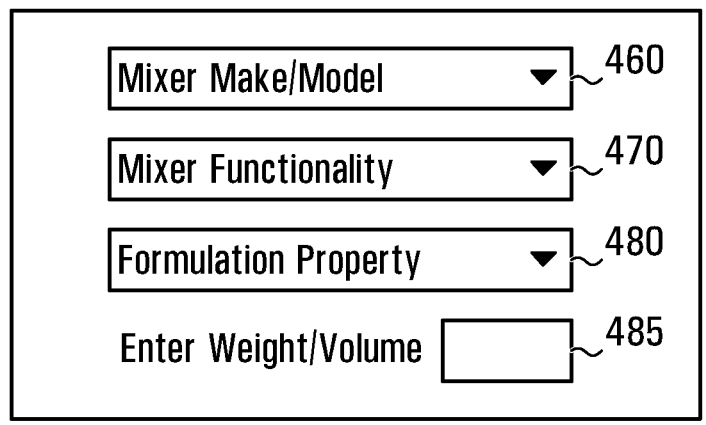
FIG. 5B illustrates a graphical user interface (GUI) on the user device that may appear during execution of the flowchart in FIG. 5A, in accordance with a non-limiting embodiment.

In order to accommodate differences in the desired weight/volume of a formulation that a user may wish to prepare, the functionality of the interactive program module 250 may be altered accordingly. Reference is thus made to FIG. 5A, which shows essentially the same flowchart as in FIG. 4A, except that it includes an additional step 435, whereby the interactive program module 250 causes the GUI 290 to display a graphical element 485 (e.g., a dialog box or menu; see FIG. 5B) that prompts the user to enter a desired weight/volume. Once the user has made all the appropriate selections via graphical elements 460, 470 and 480, including the desired weight/volume via graphical element 485, the interactive program module 250 may have enough information to obtain an actual SOP file, which is done at step 440*. In particular, the interactive program module 250 consults the SOP table 350* in order to identify the appropriate one of the records 350A* . . . 350E*.

In some embodiments, the interactive program module 250 may restrict the desired weight/volume (as entered by the user via the graphical element 485) to only those nominal weights/volumes of the records 350A* . . . 350E* in the SOP table 350*. This will guarantee that obtaining the SOP file at step 440* involves a match between the desired weight/volume and the information in the nominal weight/volume field 352W of a particular one of the records 350A* . . . 350E*.

However, in some cases, it is permissible that the desired weight/volume entered by the user via the graphical element 485 not correspond to the nominal weight/volume of one of the operating procedures in the SOP table 350*. In this case, the interactive program module 250 may carry out a comparison in order to identify the record with the closest matching nominal weight/volume to the desired weight/volume, and to retrieve the corresponding SOP file from memory. Alternatively, the interactive program module 250 may be configured to generate a customized SOP file based on the desired weight/volume and the nominal weight/volume. The customized SOP file may include scaled or interpolated quantities for the weight or volume of the ingredients used as well as the operating parameters (e.g., rotation speed, revolution speed, time, etc.). A table stored in the memory 220 may include conversions between operating parameters for different weights and volumes of a particular formulation. In this regard, further information on the formulaic generation of operating procedures can be found in U.S. patent application Ser. No. 15/809,636, filed Nov. 10, 2017, which is hereby incorporated by reference herein.

In cases where the entity that maintains the server 16 is not only a supplier of SOP files for the mixer 10, but is also a supplier of ingredients used in mixing, additional information pertaining to the account holders is available to this entity. This additional information may also be stored in the database 18. This is conceptually illustrated in FIG. 3D, where there is shown a table 330 of records 330A . . . 330D, hereinafter referred to as a "sales table". Each of the records 330A . . . 330D in the sales table 330 includes a plurality of fields, including an account #field 332A and a plurality of purchased ingredient quantity fields 332B, 332C, 332C, 332E. For a given one of the records 330A . . . 330D, the entry in the account #field 332A is information corresponding to a particular account holder associated with that record, as previously described (e.g., it could be a unique account number or customer name or legal entity name). As for the purchased ingredient quantity fields 332B, 332C, 332D, 332E, each of these fields may pertain to a different item that has been purchased by the account holder in question.

The granularity with which the purchased ingredients are designated by the purchased ingredient quantity fields 332B, 332C, 332D, 332E depend on the record keeping practices of the supplier. At a very coarse level, the purchased ingredients designated by the purchased ingredient quantity fields 332B, 332C, 332D, 332E may be categorized as base, chemical, color, flavor, oil, excipient powder, tablets and capsule, for example. At a finer level of granularity, each of the aforementioned categories could be expanded, in some cases down to the molecular level (e.g., Acesulfame Potassium, Acetaminophen, Acetazolamide, etc.). As such, the number of purchased ingredient quantity fields 332B, 332C, 332D, 332E may be very large when it is desired to keep detailed records on the purchasing history of account holders. It will be appreciated that the sales table 330 may further store the purchasing timeline of the various items purchased by the various account holders.

It will be appreciated that the credential table 310 and the sales table 330 could be merged, as each includes a respective account #field, which could refer to the same account holder.

Figure 6:
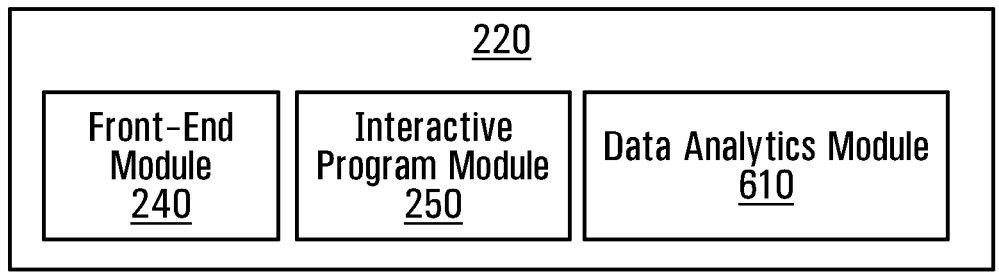
FIG. 6 is a block diagram showing example contents of the memory of the server, including a data analytics module, in accordance with a non-limiting embodiment.
Figure 7:
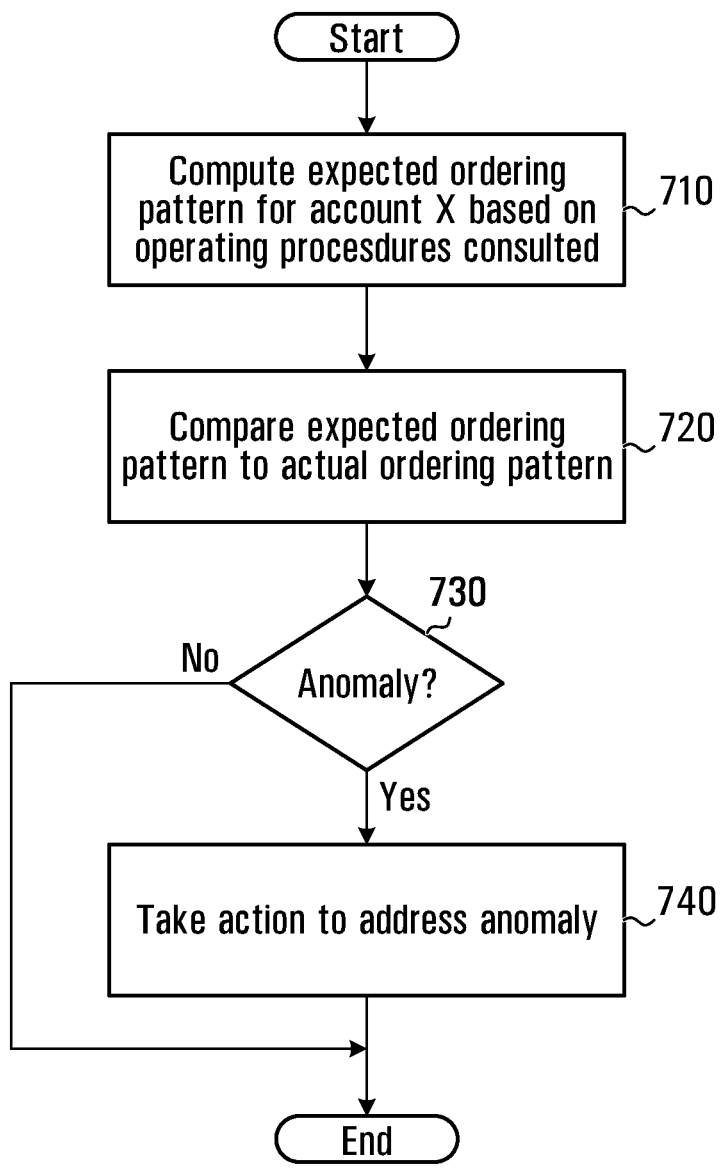
FIG. 7 is a flowchart illustrating steps that may be taken in executing the data analytics module, in accordance with a non-limiting embodiment.

The information in the credential tables 310 and the sales table 330 may have value in terms of data analytics and marketing, as will now be discussed. Specifically, with reference to FIG. 6, there is shown a data analytics module 610 that may be implemented by the server 16, namely as a result of the processor 210's execution of computer-readable instructions stored in the memory 220. The data analytics module 610 is configured to monitor the data in the credential tables 310 and the sales table 330, and to carry out a process that is now illustrated with reference to FIG. 7, performed for a particular account holder X.

Specifically, at step 710, the data analytics module 610 computes an expected ordering pattern for account holder X. This can be done by consulting the usage table 370 which, it will be recalled, tracks the frequency with which the SOP files are consulted by each account holder. As part of this step, the data analytics module 610 determines which SOP files were requested. The data analytics module 610 also consults, for example, SOP table 350**, which indicates the quantities of ingredients associated with each operating procedure. This allows the data analytics module 610 to estimate or predict that a particular ingredient or set of ingredients should have been purchased by the account holder, if the steps in the requested SOP files were actually carried out; this is referred to as the "expected ordering pattern".

At step 720, the data analytics module 610 compares the expected ordering pattern to the actual history of orders placed by the account holder, as obtained from the purchased ingredient quantity fields 332B, 332C, 332C, 332E in table 330. As part of this step, the data analytics module 610 determines, for example, the extent to which the account holder has ordered, within a period of time (e.g., the last 6 months) the ingredients that should have been purchased by the account holder as determined at step 710.

At step 730, the data analytics module determines whether there is an "anomalous ingredient supply condition". This could involve comparing, and assessing a level of discrepancy between, the ordered ingredients and the expected ordering pattern, for one or more ingredients. For this purpose, arithmetic or statistical techniques could be used. If there is no anomalous ingredient supply condition, no specific action needs to be taken. However, if there is an anomalous ingredient supply condition, such as ingredients that were purchased in a quantity less than would have been expected based on the expected ordering pattern, the data analytics module 610 proceeds to step 740. At this stage, the data analytics module 610 may prompt the account holder to order the ingredients, or may generate an alarm message. This alarm message may be sent to the entity that controls the server 16, or to any third party, signaling the anomaly.

This could then result in a sales call or other offer being electronically triggered and delivered to an address associated with the account holder.

Of course, without knowledge that the mixer 10 was used to carry out the operating procedures and without knowing how many times the steps in the SOP files were actually performed, the knowledge gained by the data analytics module 610 may be imperfect. However, if the mixer 10 itself is configured to store the SOP table 350 and is also configured to track the rate at which different SOP files are carried out, and if this information is fed back to the data analytics module 610 (e.g., over the data network 14), this can be a powerful tool to estimate the replenishment needs of the account holder and/or may provide new marketing opportunities for the supplier of ingredients. The aforementioned functionality is rendered possible when the mixer 10 is of the network-enabled variety.

Figure 8:
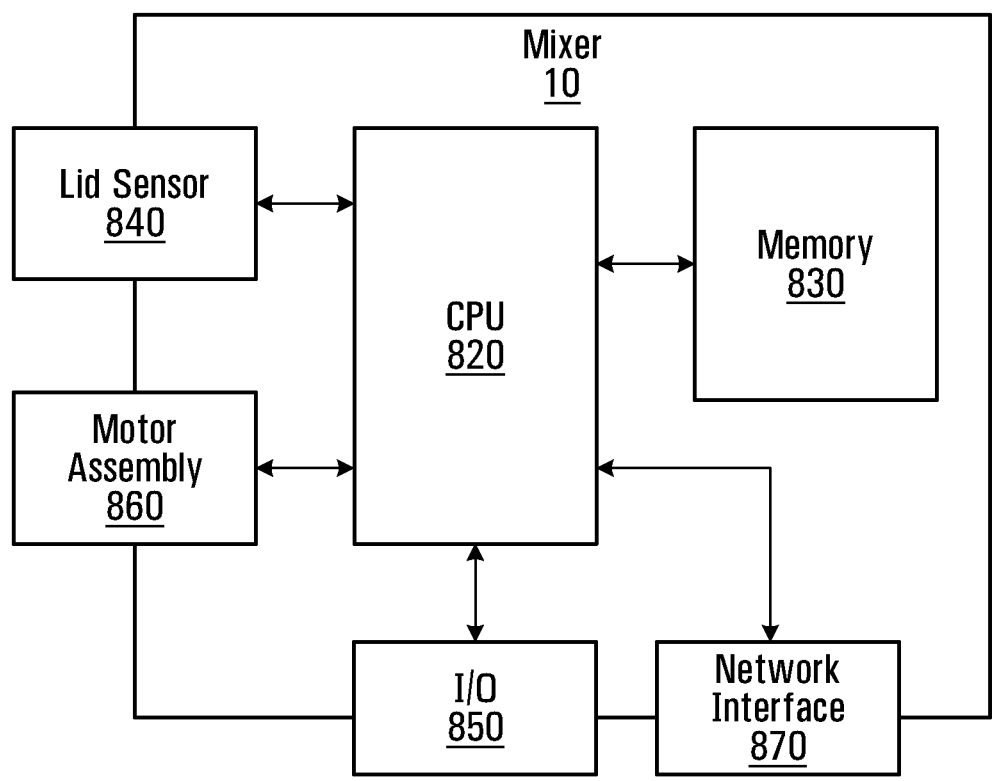
FIG. 8 is a block diagram showing components internal to the mixer, in accordance with a non-limiting embodiment.

As such, in the following embodiments, the mixer 10 is now assumed to be provided with functionality to communicate data over a network (e.g., network 14). Reference is now made to FIG. 8, which shows various components of the mixer 10 wherein the mixer 10 is network-enabled. In particular, there is shown a control and processing unit (CPU) 820, a memory 830, a lid sensor 840 (to detect whether the mixer 10 is closed or open) and a motor assembly 860. Also shown are an input/output interface (I/O) 850 (such as a screen display with key/button input) and a network interface 870. The CPU 820 executes computer-readable instructions stored in the memory 830 of the mixer 10 to process received signals from the lid sensor and to produce signals to control the motor assembly 860, for example. As an example, if the lid sensor 840 determines that the mixer 10 is open, the CPU 820 can prevent the motor assembly 840 from applying rotation and revolution. As another example, if the lid sensor 840 determines that the mixer 10 is closed, the CPU 820 can enable the motor assembly 840 to apply rotation and revolution.

The network interface 870 enables the CPU 820 to communicate with an external device or system, notably with the user device 12 (see FIG. 11) and/or the server 16. The mixer 10 is connectable to such external device/system over a wired (e.g., a cable) or wireless link. It should be appreciated that the communication link between the network interface 870 and the user device 12 and/or the server 16 may be direct (e.g., Bluetooth pairing, USB, . . . ) or it may be indirect (e.g., over the data network 14 or a LAN, by way of an Ethernet cable or wireless access point, for example).

Figure 9:
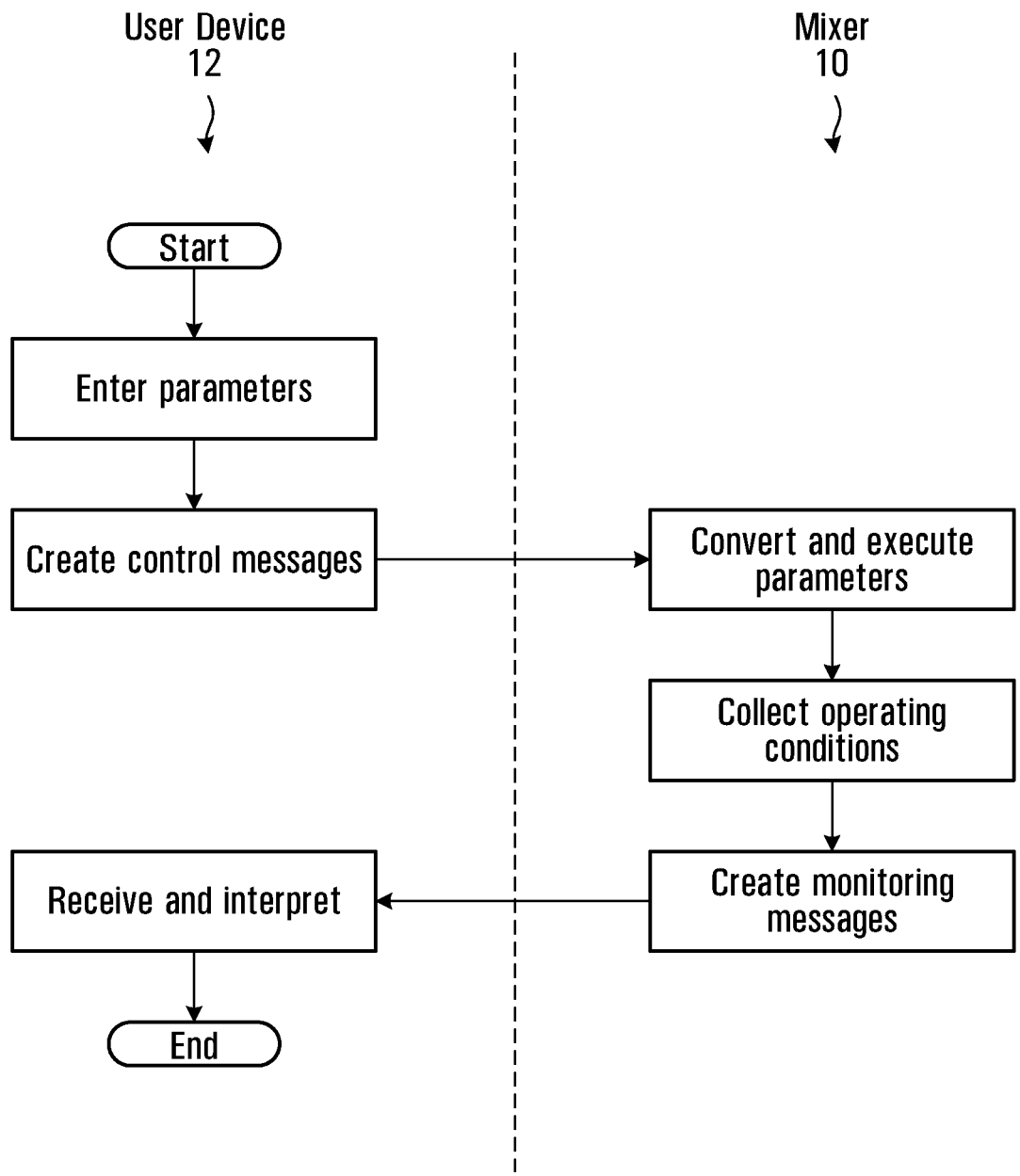
FIG. 9 is a flow diagram showing interaction between the user device and the mixer, in accordance with a non-limiting embodiment.

With reference also to FIG. 9, control messages travel from the user device 12 over the direct or indirect communication link and are received at the network interface 870 and processed by the CPU 820. These control messages may contain operating parameters as described above. Specifically, the mixer CPU 820 receives the control messages via the network interface 870, extracts the operating parameters contained therein, and acts on them, resulting in control of the motor assembly 860 so as to operate the mixer 10 in accordance with the operating parameters contained in the control messages.

In the opposite direction of communication, the CPU 820 is configured to collect information about usage of the mixer 10 (e.g., from the lid sensor 840 and also from internal sensors such as a clock, RPM sensor, . . . ), encapsulate this information into monitoring messages, and send the monitoring messages to the user device 12 via the network interface 870.

Figure 21:
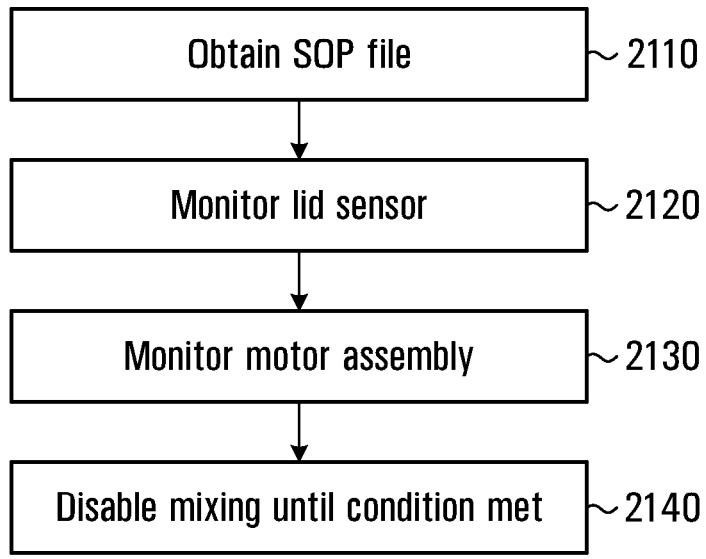
FIG. 21 is a flowchart showing steps in a process that may be carried out by the planetary mixer, in accordance with a non-limiting embodiment.

In an embodiment, the CPU 820 may execute the method shown in FIG. 21, whereby at step 2110, the CPU obtains a computer-readable SOP file associated specifying a procedure for compounding a pharmaceutical formulation using the mixer 10. The CPU 810 may obtain the SOP file by consulting a memory of the mixer 10, and/or may obtain the SOP file from the user device 12 or the server 16. In this example, the SOP file specifies at least: a suggested first mixing step, a suggested second mixing step, and a step intermediate the suggested first and second mixing steps requiring the container to be removed from the planetary mixer. Then, at step 2120, the CPU 820 monitors the lid sensor 840 of the mixer 10 to determine whether the mixer 10 is open or closed. At step 2130, the CPU 820 monitors the motor assembly 860 of the mixer 10 to determine that an actual first mixing step corresponding to the suggested first mixing step has been completed. Finally, at step 2140, the CPU 820 disables further mixing by the motor assembly until the monitoring (at step 2130) determines that the mixer has been opened after completion of the actual first mixing step.

Figure 11:
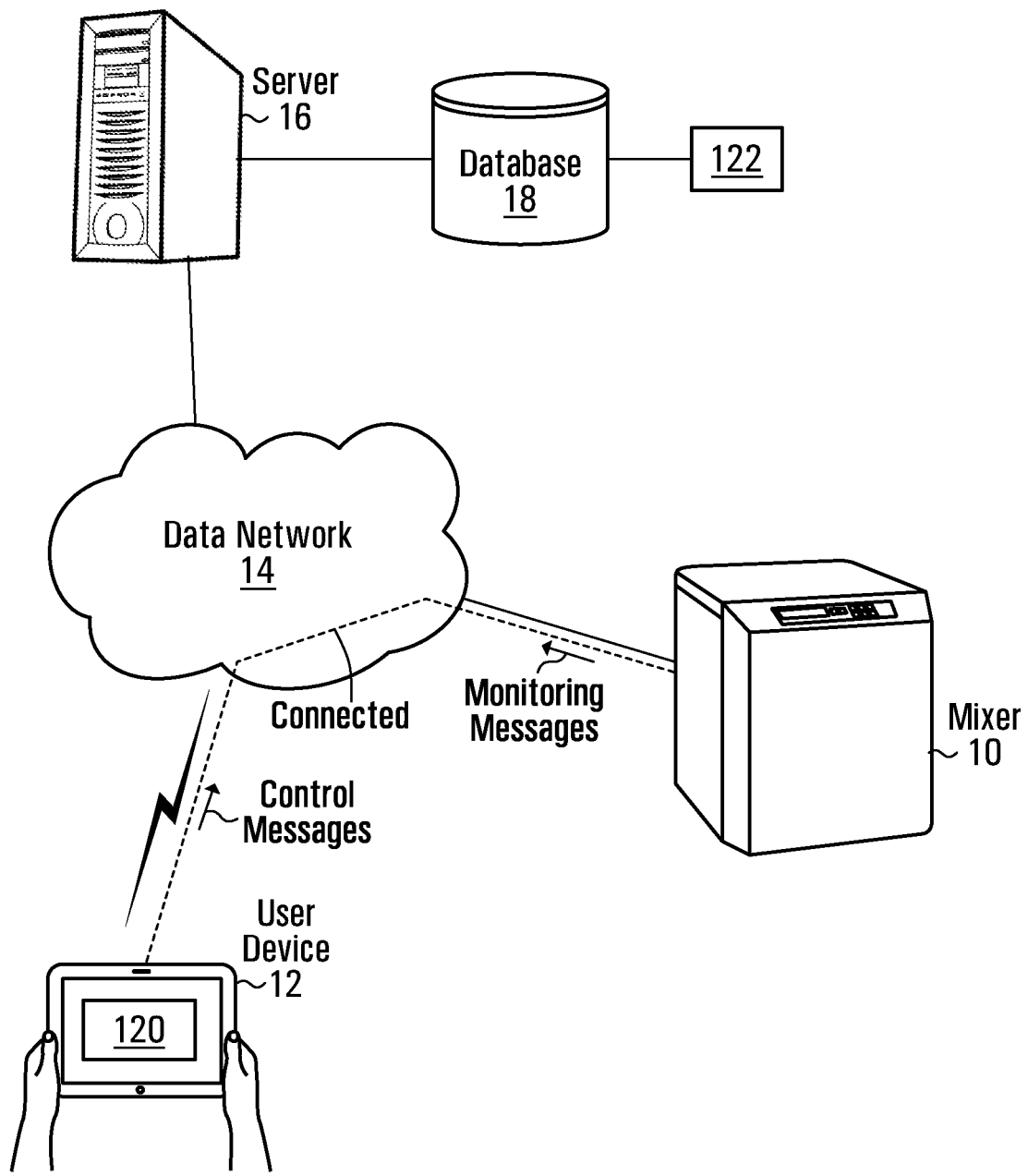
FIG. 11 illustrates the mixer ecosystem system of FIG. 1 in which the mixer is connected to the data network, in accordance with a non-limiting embodiment.

For its part, and with continued reference to FIG. 11, the user device 12 executes a mixer control application 120 to formulate and send control messages (containing operating parameters) to the mixer 10. In other words, the mixer control application 120 can encode the operating parameters into the control messages. The mixer control application 120 may be one of the processes that is executed by the user device 12 as a result of the execution of computer-readable instructions stored in the memory of the user device 12. In one embodiment, the mixer control application 120 may allow a user to enter operating parameters which are then converted into control messages and transmitted to the mixer 10. For example, the user enters operating parameters such as "30 seconds at 2000 rpm" via the GUI implemented by the user device 12. In another embodiment, the mixer control application 120 obtains operating parameters from a memory of the user device 12 or from an external device or system, such as the server 16, over the data network 14. The mixer control application 120 converts these operating parameters into control messages in accordance with a protocol understandable by the mixer 10.

Also, the mixer control application 120 receives and processes monitoring messages from the mixer 10. The collected monitoring messages can be used by the mixer control application 120 for various purposes, such as to signal the need for preventative maintenance. Specifically, the mixer control application 120 may be configured to upload collected usage information to the server 16. The server 16 can then provide "preventative maintenance" detection functionality, as well as data analytics. In an example, the data analytics module 610 at the server 16 can be used to track precise usage and performance issues for an individual machine or over an entire fleet of mixers. This allows precise detection of anomalous ingredient supply conditions, discussed above. In another example, the data analytics module 610 at the server monitors how many hours the mixer has been used and comparing against a table 122 supplied by the manufacturer. This table 122 can be stored in the database 18 or in the memory 220 of the server 16, and may indicate a suggested or number of hours of use after which maintenance should be performed on the mixer 10. In this case, the output of the data analytics module 610 may be an indication as to whether mixer maintenance is recommended.

In some scenarios, the user may be interested in using the mixer 10 to make a formulation consisting of two or more ingredients combined in relative proportions defined by a formula. To this end, the user may be interested in knowing the operating parameters for making a particular formulation, given the corresponding formula (i.e., the list of ingredients and their relative quantities) and the total quantity/volume. These operating parameters are to be supplied to the mixer 10. It is noted that this can be viewed as a radically simplified version of an operating procedure, equivalent to an operating procedure consisting of a single process step that involves supplying to the mixer 10 specific operating parameters associated with a specific formula (and possibly a total weight or volume).

Accordingly, and with reference to FIG. 12, a formula database 1210 associates formulas to operating parameters. As such, the database 1210 is illustrated as having rows corresponding to formulas, where the row corresponding to a particular formula has an entry for the associated operating parameters. Although it is feasible to have a single set of operating parameters for a given formula, it is possible for the operating parameters to vary as a function of the total weight of the eventual formulation. As such, the formula database 1210 is illustrated as having rows corresponding to different formula and weight combinations, where the row corresponding to a particular formula and weight combination has an entry for the associated operating parameters. Further options for a given formula (or formula and weight combination) could be obtained, for example, based on other factors such as the absolute weight of a particular ingredient in the formula, altitude above sea level, temperature, mixer make/model, and so on. In fact, there could be a curve that captures the variance in operating parameters (e.g., rotation RPM, revolution RPM and mixing time over one or more intervals) as a function of each factor, so that depending on the value of the factor, the optimal operating parameters are obtained. The formula database 1210 may be updated as new formulas are developed and tested with the mixer 10.

Depending on the embodiment, the formula database 1210 may be stored in the memory of the server 16, in the memory of the user device 12 or in the memory of the mixer 10.

Figure 13A:
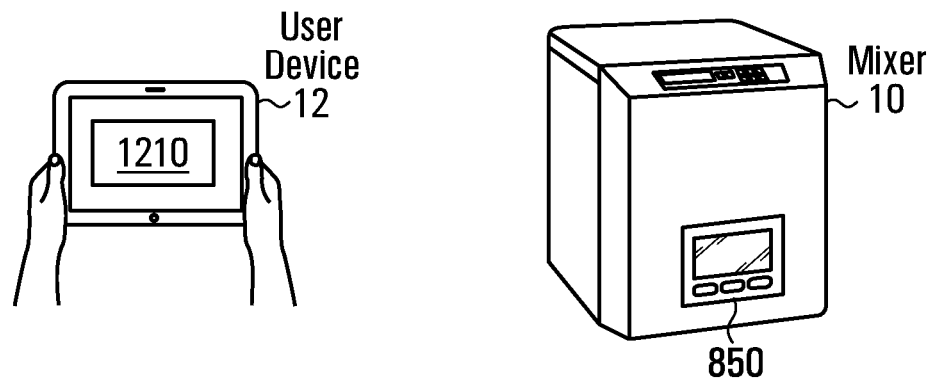
FIGS. 13A to 13C illustrate the user device and the mixer in various degrees of interconnectedness, in accordance with a non-limiting embodiment.

As such, according to a first variant, shown in FIG. 13A, the mixer 10 is stand-alone (i.e., it does not require networking functionality) and the formula database 1210 resides in the memory of the user device 12. The user enters a desired formula on the user device 12. One way is for the user device 12 to list the actual ingredients corresponding to the desired formula and their relative proportions. Another way is for the user device 12 to provide a menu of formulas from which the user may make a selection of the desired formula. Yet another way is for the user to submit a pre-determined code (or "preset") that is recognized by the user device 12; this preset can be a code selectable by the user from a menu or scannable by a scanner connected to or integrated with the user device 12. The user device 12 may include a table in memory that maps presets to formulas. In some embodiments, the user may also enter other parameters, such as the make/model of the mixer and, e.g., the elevation above sea level where mixing is taking place. In all cases according to the present variant, the user device 12 accesses the formula database 1210 and obtains the associated operating parameters, displaying them on the screen of the user device 12. Thereafter, according to the present variant, the user manually enters the obtained operating parameters via the user interface 850 of the mixer 10.

Figure 13B:
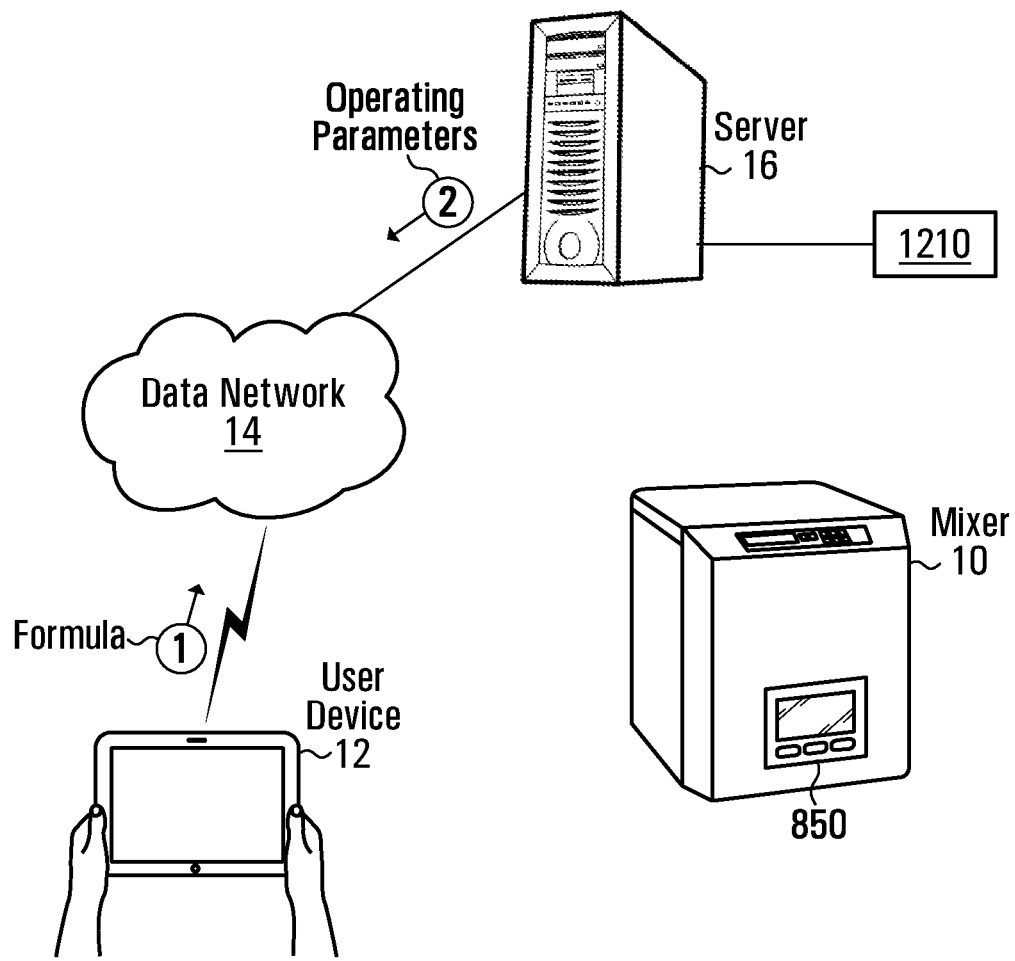

According to a second variant, shown in FIG. 13B, the mixer 10 is still stand-alone, however the formula database 1210 resides on the server 16. The user enters a desired formula on the user device 12 in one of the above ways, and the user device 12 contacts the server 16 over the data network 14 and accesses the formula database 1210. The server 16 returns the associated operating parameters. The user device 12 displays the operating parameters on the screen of the user device 12, and the user can then manually enter the obtained operating parameters via the user interface 850 of the mixer 10.

Figure 13C:
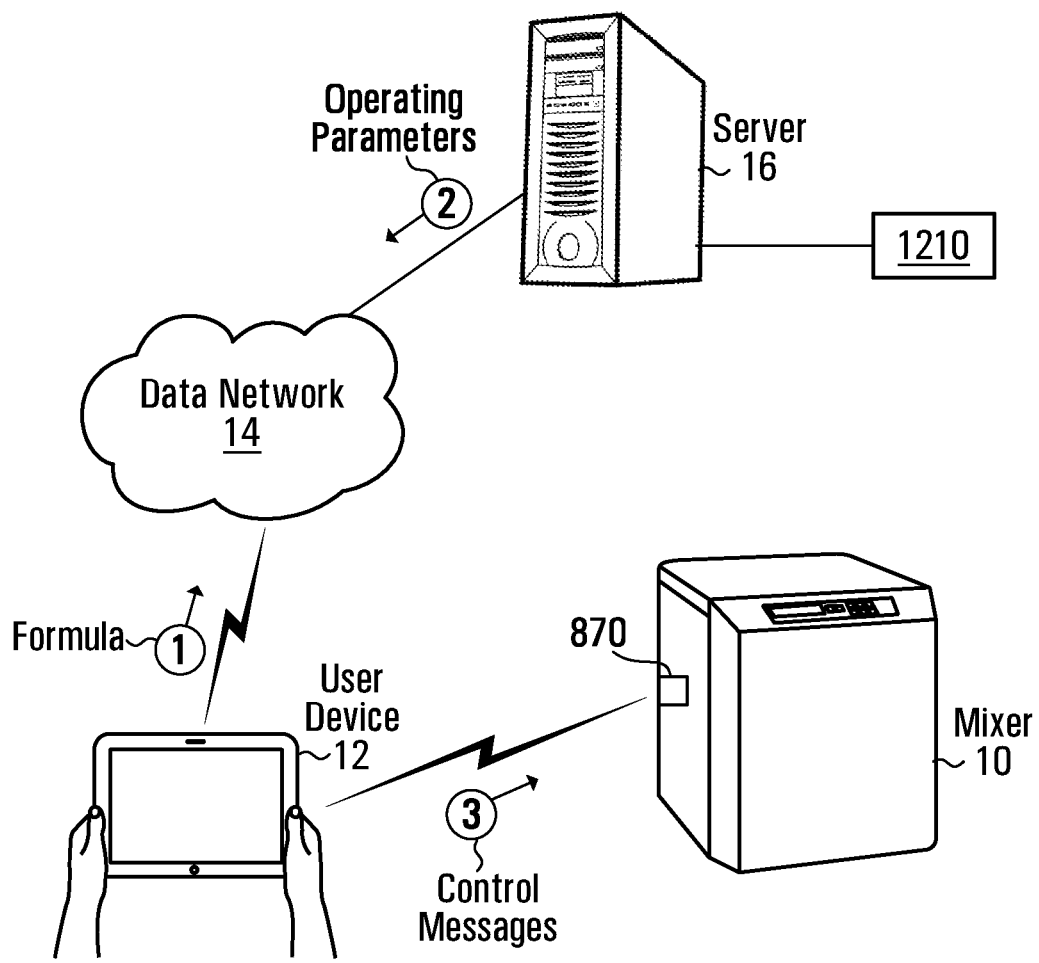

According to a third variant, shown in FIG. 13C, the network functionality of the mixer 10 is enabled, and the formula database 1210 resides on the server 16. The user enters the formula on the user device 12 in one of the above ways (including, for example, by selecting a preset), and the user device 12 contacts the server 16 over the data network 14 and accesses the formula database 1210. The server 16 returns the associated operating parameters. (Alternatively, the formula database 1210 could reside in the memory of the user device 12, in which case the server 16 need not be contacted.) The user device 12 then encapsulates the operating parameters into one or more control messages that is/are sent to the mixer 10 and received at the network interface 870. Optionally, the operating parameters are also displayed on screen of the user device 12.

Figure 13D:
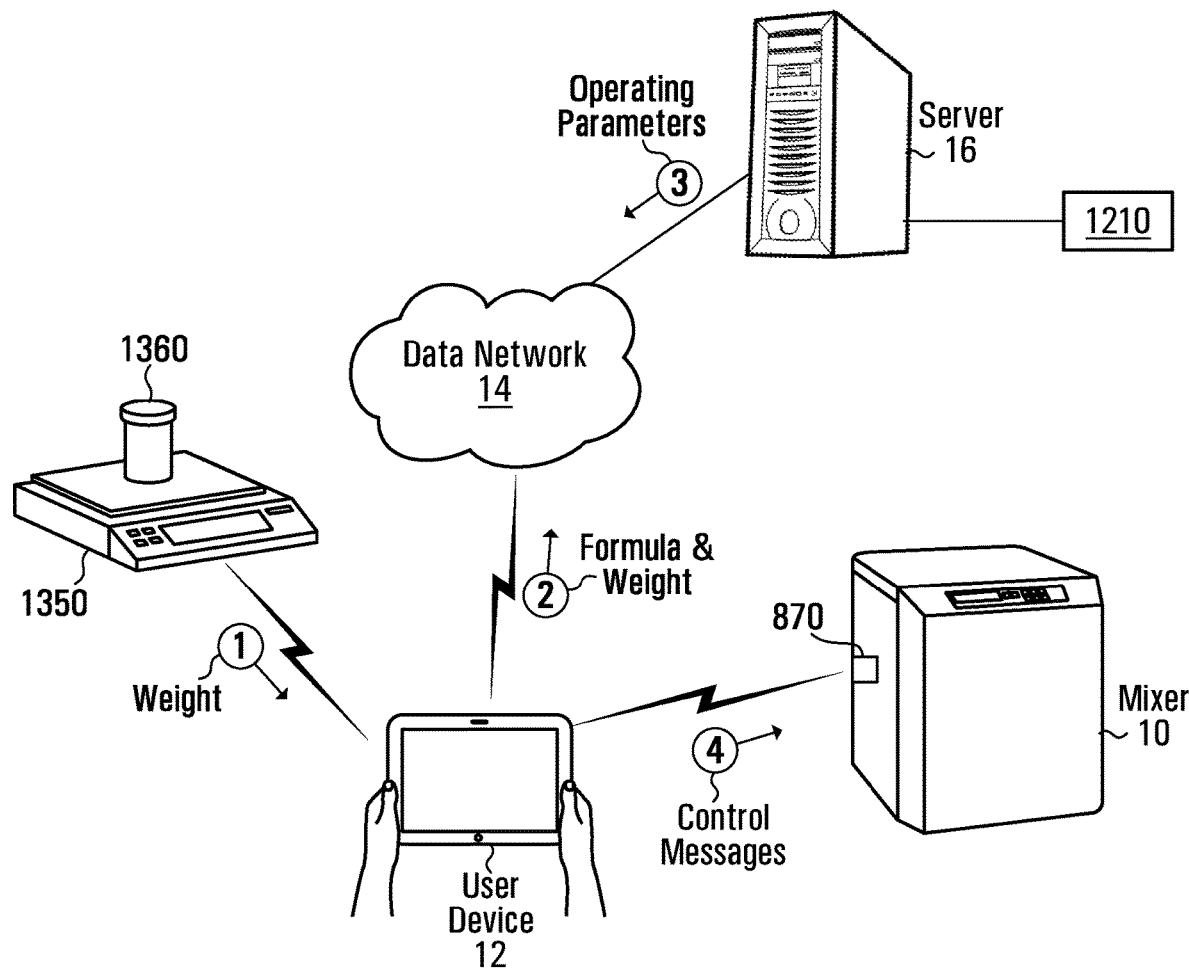
FIG. 13D is a variant of FIG. 13C, further including a scale, in accordance with a non-limiting embodiment.

According to a fourth variant, shown in FIG. 13D, the network functionality of the mixer 10 is enabled, and there is provided a scale 1350. In this variant, the user places a container 1360 containing the ingredients onto the scale 1350 and enters the corresponding formula on the user device 12 in one of the above ways. The user device 12 reads the scale 1350 to obtain a weight, then accesses the formula database 1210, which could be in the memory of the user device 12 or accessible over the data network 14. This approach may be particularly suitable when the particular formula database 1210 has varying operating parameters for different total formulation weights, even for the same formula. Once the operating parameters are received, the user device 12 places the operating parameters into one or more control messages that is/are sent to for the mixer 10. Optionally, the operating parameters are also displayed on the screen of the user device 12. According to this variant, the user basically adds ingredients to the container 1360 according to a formula, selects the formula via a graphical user interface on the user device 12, and presses "start". The remaining operations are automated.

According to a similar variant, the user places a container 1360 containing the ingredients onto the scale 1350 and enters the corresponding formula via a graphical user interface on the mixer 10. The mixer 10 reads the scale 1350 to obtain a weight, then accesses the formula database 1210, which could be in the memory of the mixer 10 or accessible over the data network 14. Here, the user adds ingredients to the container 1360 according to a formula, selects the formula via a graphical user interface on the mixer 10, and presses "start". The remaining operations are automated.

In yet another variant, the user provides a code (e.g., a scannable code) to the user device 12. The code encodes the operating parameters. The code may be part of a "formula sheet" for the desired formula. As such, if the user desires to make the desired formula, a formula sheet may be obtained, and this formula sheet may include a code that is scanned by a scanner. The formula sheet may be printed or digital. The code may include a plurality of fields, and collectively defines the operating parameters that may have been optimized for the mixer 10. For example, a scannable code may read:
  004520001000, or equivalently
  0045-2000-1000, which could be interpreted to mean 45 seconds at 2000 rpm rotation and 1000 rpm revolution, for example. Other constructions of the code, including more complex ones, are of course possible. For example,
  003020000050000500401000015 0, or equivalently
  0030-2000-0050-0005-0040-1000-0150, could be interpreted to mean (0030=30) seconds at (2000=2000) rpm rotation and (0050=0.5)×2000 rpm revolution, followed by a pause of (0005=5) seconds, and then mixing resumes for (0045=45) seconds at (1000=1000) rpm rotation and (0150=1.5)×1000 rpm revolution. In this case, the 3rd and 6th fields represent a ratio of rotation rpm to revolution rpm.

Using this approach, the user device 12 reads the scannable code from the (printed or digital) formula sheet to directly obtain the operating parameters, which are then sent as control messages to the mixer 10. In an alternate embodiment, the mixer 10 acts as the user device and is equipped with a scanner and is configured to directly decode the operating parameters from a scannable code.

In some variants, the code may be encrypted when produced and provided on a formula sheet (either printed or digital) so that it may only be decrypted by a suitable user device or mixer. For example, if the code specifies operating parameters that have been optimized for a particular make/model of mixer, a public/private key system infrastructure may be used to encrypt the operating parameters with a public key associated with the appropriate make/model of mixer. Meanwhile, the private key is secretly held by the mixer of the appropriate make and model. As such, only the appropriate make and model of mixer will be able to correctly decrypt the code and obtain the operating parameters that were initially associated by the creator of the formula sheet. Other makes or models of mixers, even if they are configured to directly read operating parameters from a code on a formula sheet, will be unable to decrypt the correct operating parameters without the correct private key, which is held secret by the mixer (or mixers) of the appropriate make and model. The code may furthermore be affixed to a mixing container, such that simply scanning the code will immediately provide the user device 12 and/or the mixer 10 with the correct operating parameters. Thus, the user device 12 and/or the mixer 10 simply needs to be fitted with the capability to interpret a limited number of fields of the code (and possibly a decryption capability); in this case there may be no need to store or access a formula database such as the formula database 1210. Since the number of fields of the code is much less than the number of possible formulas, this may be an effective way to directly convey to the user device 12 and/or the mixer 10, in an error-free way, instructions on how to operate, and without the user device 12 having to store or access a large table that maps formulas to operating parameters.

Once the mixer 10 has finished the mixing operation defined by the operating parameters entered into the mixer 10 in one of the above ways, the mixer 10 may be configured to send a completion message to the mixer control application 120 over the wired or wireless connection. In this way, the mixer control application 120 is alerted that mixing has terminated. In embodiments where the mixer 10 is connected to the data network 14, this allows the user to carry the user device 12 into another room or facility and to be alerted, over the data network, that the mixing operation has finished. The completion message can be in the form of an email or text message sent to a pre-defined number or address, or an audible or visual on-screen alert.

In some embodiments, the interactive program module 250 has intelligence in order to reduce the occurrence of errors in the carrying out of an operating procedure. That is to say, instead of only supplying an SOP file to a requestor, the interactive program module 250 may be configured to require confirmation that the various steps in the SOP file are being performed correctly. For example, the interactive program module 250 may be configured to compare the operating parameters used actually and the operating parameters suggested by the SOP file, and taking an action, such as issuing an alarm, that depends on a result of the comparison. In a simple example, the interactive program module 250 may be configured to signal an alarm if a threshold amount of time has elapsed between steps. Such an alarm may be a visual alarm signal sent via a user interface of the mixer 10. In some cases, where the mixer 10 is a stand-alone device, the interactive program module 250 has no way of knowing whether the user has actually complied with any of the individual process steps of the SOP file. However, if the mixer 10 is connected to the server 16 (e.g., via the data network 14, or via the mixer control application 120 running on the user device 12), the interactive program module 250 may have access to monitoring messages from the mixer 10. These monitoring messages may indicate the status of the mixer 10, whether the lid is open or closed, the values of the operating parameters being supplied to the mixer 10 and so on. This can allow the interactive program module 250 to corroborate whether the steps in the SOP file have been correctly performed, which may potentially reduce errors.

For example, one of the process steps in the SOP file may require the user to remove the container from the mixer 10 in order to perform some action, such as add a wetting agent or further ingredient, and then to return the container to the mixer 10. In this case, based on monitoring messages received from the mixer 10, monitoring the state of the lid would allow the interactive program module 250 to determine whether this process step was being correctly followed.

The aforementioned interaction carried out by the interactive program module 250 may also be carried out by the mixer control application 120 running on the user device 12, provided that the SOP file has been obtained and stored in memory.

Even more sophisticated ways to avoid human error may involve keeping track of which ingredients are added to the container. In some embodiments, the mixer control application may be configured to validate the collected data before authorizing the mixer 10 to be started.

For example, it may be possible to explicitly track the ingredients being added to a container so as to gain improved quality control and/or business insight. In this regard, it is noted that many ingredients approved for use in a pharmacy setting are associated with a unique CAS number (a unique numerical identifier assigned by the Chemical Abstracts Service (CAS) to every chemical substance described in the open scientific literature). CAS numbers can appear on the bottles and containers of the various ingredients to be used in creating the formulation of choice. The CAS numbers may even be encoded in a bar code or QR (quick response) code on the various ingredient containers.

Figure 10:
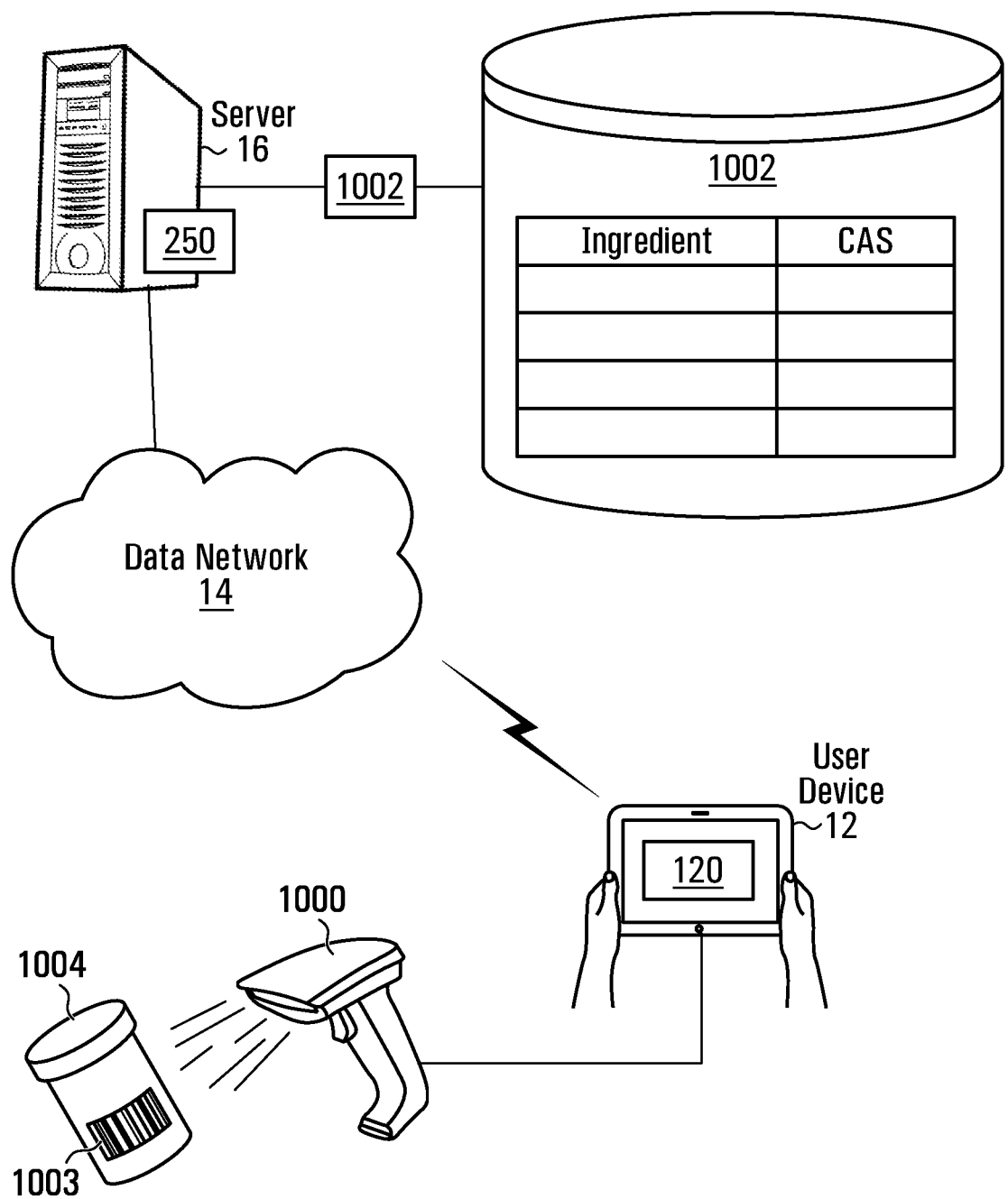
FIG. 10 is a block diagram showing entities participating in a validation process, in accordance with a non-limiting embodiment.

In accordance with an embodiment, and with reference to FIG. 10, there is provided a data entry device 1000, which could be a keyboard, scanner (including, but not limited to, a bar code scanner), etc. connected to the user device 12 running the mixer control application 120. The data entry device 1000 may be used to input/acquire the CAS number of an ingredient that a pharmacist is adding to the container in which mixing is to occur. This can be done by scanning a bar code or QR code 1003 in a particular region of a container 1004 containing the ingredient. It is assumed that the mixer control application 120 has obtained a particular SOP file (e.g., from the interactive program module 250) specifying or encoding a plurality of process steps, at least one of which involves mixing certain ingredients in certain proportions. As such, the SOP file lists one or more ingredients. In addition, the mixer control application 120 has access to a database 1002 of CAS numbers associated with various possible ingredients, including those listed in the SOP file. Access to the database 1002 may be provided over the data network 14.

Figure 20:
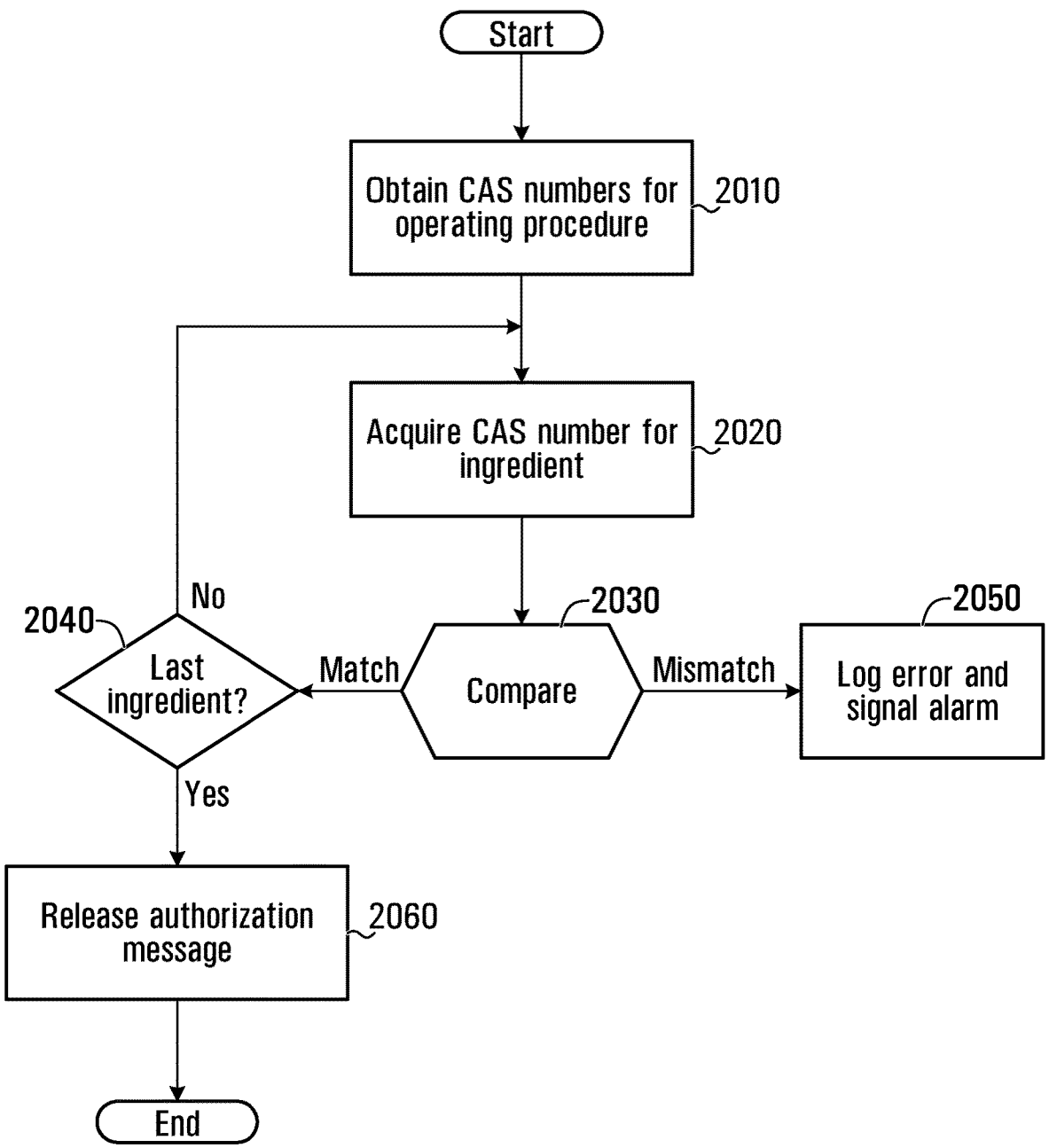
FIG. 20 is a flowchart showing steps in a validation process, in accordance with a non-limiting embodiment.

In this embodiment, the mixer control application 120 executes a validation process, steps of which are shown in the non-limiting flowchart of FIG. 20. Optionally, the mixer control application 120 may be configured to disable the mixer 10 from mixing until the validation process has successfully completed. An initialization step 2010 may be provided, whereby the mixer control application 120 contacts the database 1002 to obtain the CAS numbers of the ingredients associated with a desired SOP file (that may be specified by a user). At step 2020, according to the validation process, ingredient data is acquired by the data entry device 1000. This can be a CAS number or image data that encodes a CAS numbers. At step 2030, the validation process compares the acquired CAS number to the CAS numbers of the ingredients associated with the SOP file. At this point, the validation process carries out an action that depends on the result of the comparing. For example, if there is a match, then the next step could be step 2040. If there is a mismatch, i.e., one of the acquired CAS numbers does not match any of the CAS numbers for the ingredients listed in the SOP file, then the validation process may, at step 2050, log the error and also to signal an alarm in real-time, in the form of a message, audible or visual cue. This can immediately alert the preparer of the formulation that there is a problem, potentially resulting in less wastage of time and material resources. An optional step (not shown) may check to determine whether the CAS number has been duplicately scanned and, if so, to issue an alarm.

At step 2040, the validation process determines whether the acquired CAS number corresponds to the last ingredient that needed to be scanned for the selected SOP file. If so, the mixer control application 120 may, at step 2060, enable the mixer 10 to authorize it to commence mixing. This can be done my sending an authorization message to the mixer 10. Mixing may occur according to operating parameters that may be provided, as part of the SOP file, by the mixer control application 120 or by the pharmacist directly via the user interface 850 of the mixer 10. Until the authorization message is received by the mixer 10, further mixing may be blocked (i.e., the mixing functionality of the mixer 10 may be disabled). This may also improve the reliability of the compounding process. It should also be understood that the mixer 10 may be provided with a feature to override the blocking imposed on it by the mixer control application 120. For example, the mixer 10 may be configured to recognize a particular code. Thus, by entering the particular code via the user interface 850, the pharmacist can forcibly bypass any warnings issued by the mixer control application 120.

A further enhancement, which may be incorporated into the validation process, may involve a scale 1340, which can ensure that not only are the correct ingredients being added to the mixing container, but they are being added in the correct quantities and/or proportions. Specifically, scale 1340 is connected to the user device 12 and is configured to output weight measurements. The mixer control application 120 is configured to read the weight measurements made by the scale 1340. A comparison is effected between the received weight measurements and the weight that is specified in the SOP file. In some cases the SOP file does not specify the weight of each ingredient but rather the relative proportions of the weight of each ingredient. In such cases, the scale 1340 can be used to collect the weight of each ingredient being added by the pharmacist, and then the mixer control application 120 calculates the relative proportions in order to determine whether they correspond to, or are within a certain tolerance of (e.g., within 0.1%, 1% or 5%) of the relative weight proportions of the ingredients listed in the SOP file.

When the pharmacist enters a particular formulation that he/she wishes to create, the validation process can be used as one additional check to ensure that the correct ingredients are being added to the mixture. It should be appreciated that the aforementioned CAS-based system is manufacturer-agnostic, as it is expected that all products will have a CAS number. In other cases, ingredients may also have a manufacturer-specific code, such as a bar code or QR code. As ingredients are being added, the scanner can be used to scan the bar/QR code, which is then sent to the server 16, allowing the entity that owns/manages the server 16 to keep track of which pharmacies use how much of which ingredients sourced by which manufacturers. This information is valuable as it could allow the entity that owns/manages the server 16 to develop a sales strategy.

In an embodiment, it may be possible to render larger scale pharmaceutical compounding more efficient by decoupling the preparation of mixing containers from the actual mixing of those containers with a mixer, such as the mixer 10.

For example, when access to APIs or controlled substances is restricted physically or otherwise, it may be more efficient to prepare numerous containers with such APIs or substances during a first time frame ("preparation phase"), and then to mix the contents of those containers during a subsequent time frame ("mixing phase"). In other cases, a container may be prepared by one group of specialists and mixed by another group of specialists. In the aforementioned cases, there is a serious risk of error and it may be beneficial to keep track of which prepared containers contain which ingredients so as to be able to instruct the mixer 10 with the correct operating parameters.

To this end, there is proposed a tagging solution, whereby individual containers are electronically tagged. One suitable non-limiting example is a non-contact tag, such as an RFID tag. The RFID tag may comprise a memory, an antenna and a microcontroller that allows reading and writing of the memory content. The RFID tag may be a passive RFID tag, to which power must be supplied when writing to the memory, and which can be read by energizing it wirelessly from a distance, such that it releases the contents of its memory. An active RFID tag may also be used, whereby the tag includes a built-in power supply that is replenished by a battery, kinetic movement, etc.

The proposed tagging solution influences two phases of pharmaceutical compounding, referred to generally herein as a "preparation phase" and a "mixing phase".

Figure 14:
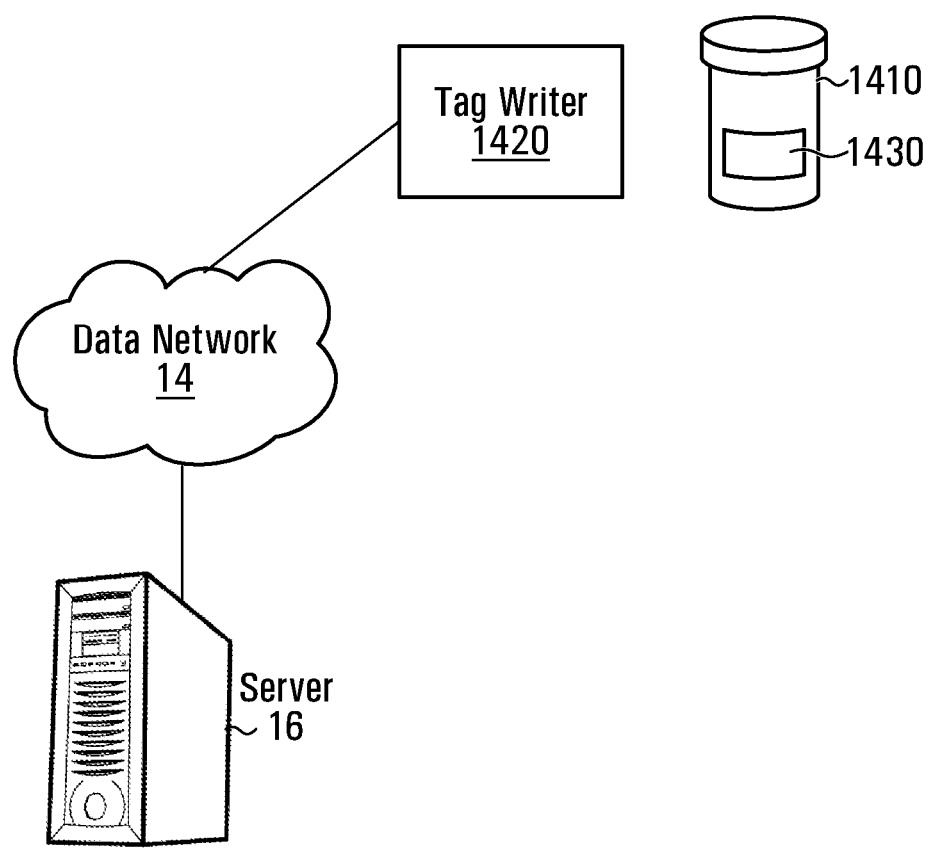
FIG. 14 is a block diagram showing a server, a tag reader and a tag-enabled container, in accordance with a non-limiting embodiment.

The preparation phase is now described. With reference to FIG. 14, there is shown a tag-enabled container 1410 and a tag writer 1420. The container 1410 includes a tag 1430 such as an RFID tag. Other devices may also be suitable, such as barcodes or devices based on NFC or Zigbee technology, for example. The tag writer 1420 may be a device that is capable of writing information to a tag such as the tag 1430 of the container 1410. The tag writer 1420 may be connected to a back-end server, such as the server 16. In one embodiment, the tag writer 1420 has a console that may be accessed by the user. In another embodiment, the user may access a separate user device (such as the user device 12) that is connected to the tag writer 1420, e.g., over a wireless or wired link. In a further embodiment, the user may use the user device 12 to connect to the back-end server (e.g., server 16) over a data network (e.g., data network 14), such as the internet. In any event, the user is assumed to be desirous of preparing a total weight/volume of a particular formulation defined by a formula, i.e., a list of ingredients in certain absolute and relative quantities. Accordingly, during the preparation phase, the user fills the tag-enabled container 1410 with the appropriate ingredients in the appropriate absolute and relative quantities, and then enables a write operation to the tag 1430 of the tag-enabled container 1410 using the tag writer 1420. The information written to the tag 1430 could be the particular formula (including, or not, the total weight/volume), or a code that is maintained in the back-end server 16 and maps to the particular formula but is meaningless to someone who does not know this mapping.

The above operations can also be done in reverse, i.e., the tag 1430 can be written to first and then the tag-enabled container 1410 can be filled. In yet another embodiment, the tag 1430 is a loose item and its memory is written to separately by the tag writer 1420, following which the loose tag is affixed to a virgin (non-tag-enabled) container, thus yielding in a tag-enabled container such as the container 1410. It may also be possible to integrate tag writing with the aforementioned validation process. For example, the tag writer 1420 can be configured to write to the tag 1430 only if the validation process has been passed successfully, and/or to write to the tag 1430 an indication of whether the validation process was passed successfully or even carried out.

The preparation phase is now complete, the result being a filled tag-enabled container 1410 whose tag 1430 is indicative of its contents, either explicitly or by way of a code.

Figure 15:
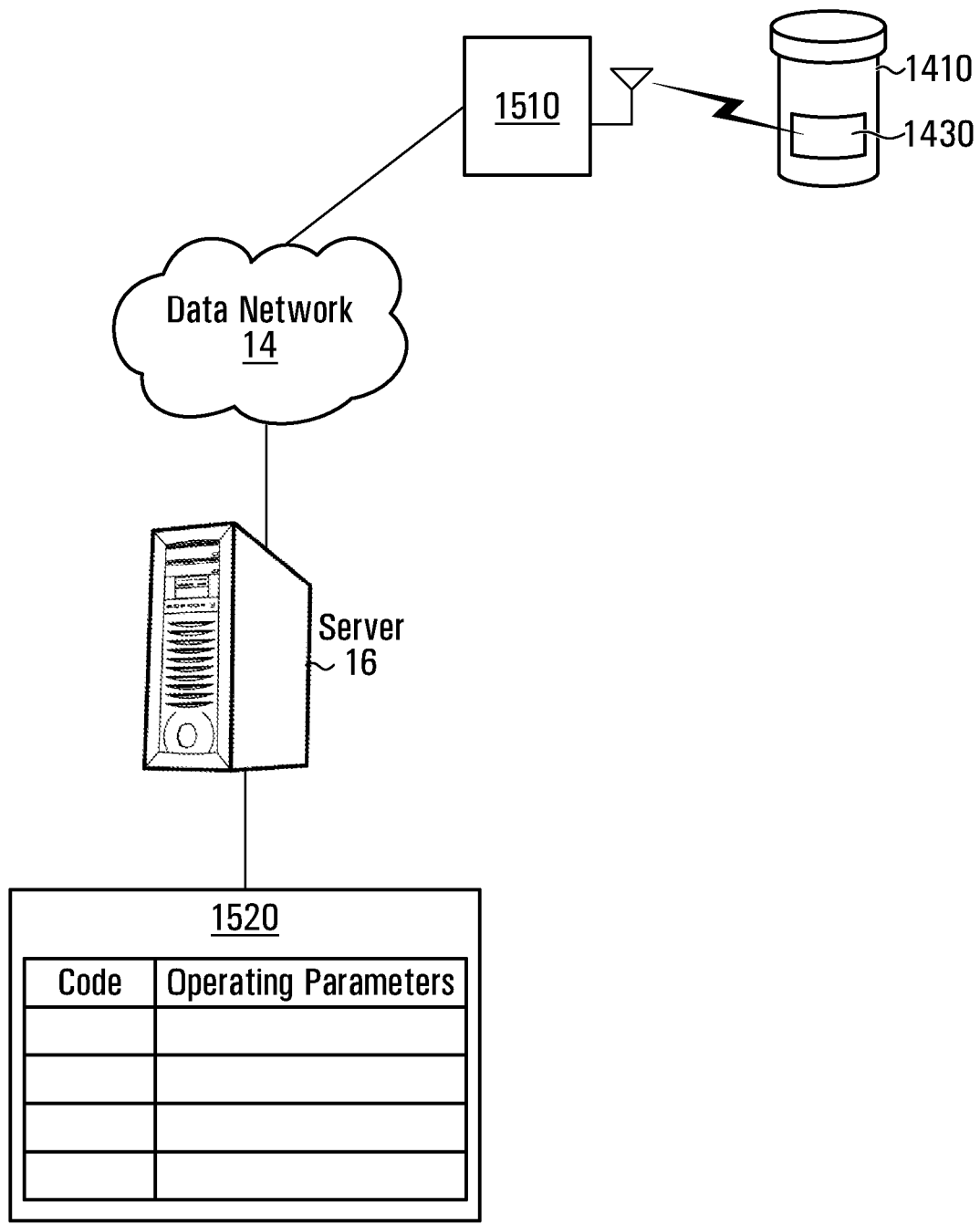
FIG. 15 is a block diagram showing the tag reader being coupled to a database containing operating parameters, in accordance with a non-limiting embodiment.

The mixing phase is now described. In particular, with reference to FIG. 15, there is shown the tag-enabled container 1410 and a tag reader 1510. The tag reader 1510 is connected to a database 1520. The database 1520 may be stored in the server 16, to which the tag reader 1510 may be connected via the data network 14. In one embodiment, which may be applicable in the case where the tag 1430 stores the contents of the container 1410 explicitly, the database 1520 stores a mapping between formulas (and possibly also total weight) and the optimal operating parameters for the mixer 10 (i.e., the database 1520 stores a table similar to table 1210). In another embodiment, which may be applicable in the case where the tag 1430 stores a code that uniquely corresponds to a formula (and possibly also total weight), the database 1520 stores a mapping between codes and sets of optimal operating parameters for the mixer 10.

In either case, the operating parameters are retrieved from the database 1520 and conveyed to the mixer 10. This can be done in a variety of ways.

Figure 16A:
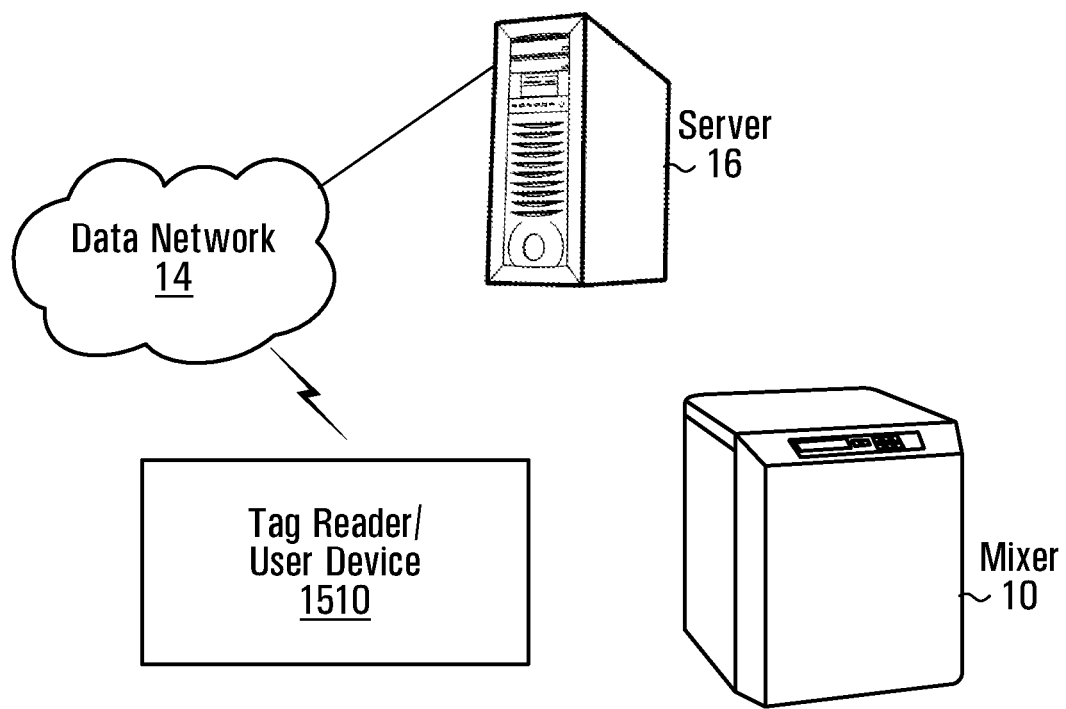
FIGS. 16A to 16C illustrate the tag reader and the mixer in various states of interconnectedness, in accordance with a non-limiting embodiment.

In a first embodiment, shown in FIG. 16A, the tag reader 1510 can be integrated with a user device (e.g., a smartphone or tablet), and the operating parameters are sent from the server 16 to the user device/tag reader for display thereon. The user then enters the operating parameters into the mixer (not shown). For this embodiment, the mixer 10 does not require an external or networked connection.

Figure 16B:
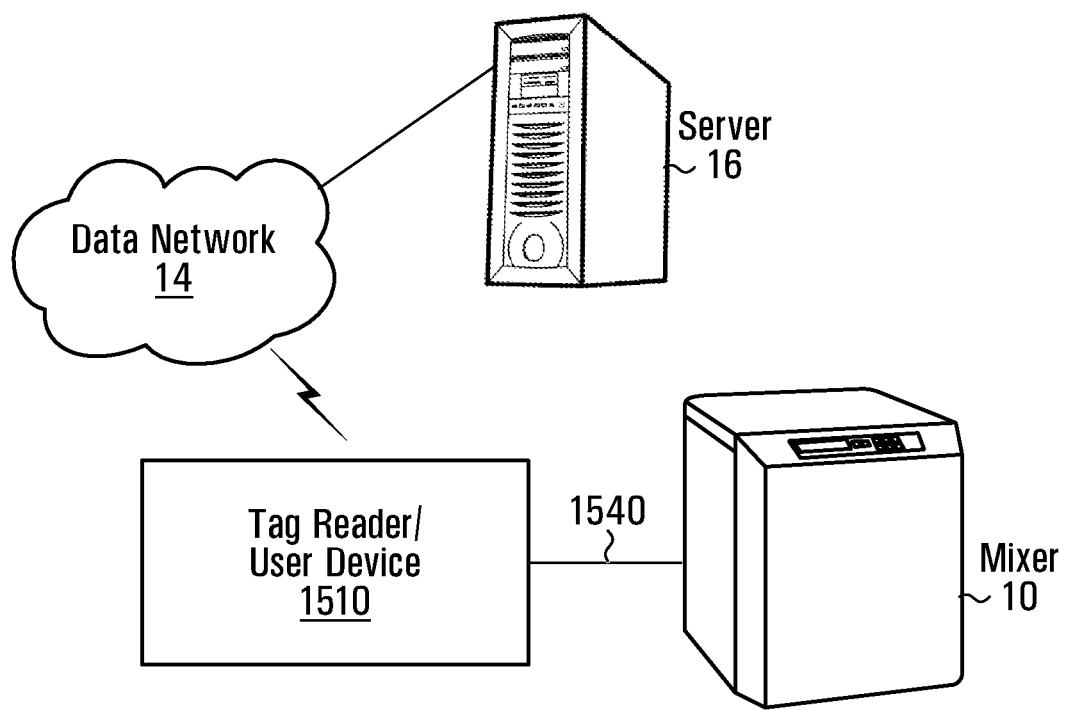

In a second embodiment, shown in FIG. 16B, the tag reader 1510 may be embodied as a separate system, and the mixer 10 has an external wired or wireless connection 1540 to the tag reader 1510. In this case, the operating parameters are sent from the server 16 to the tag reader 1510, which sends the operating parameters to the mixer 10 via the external connection 1540.

Figure 16C:
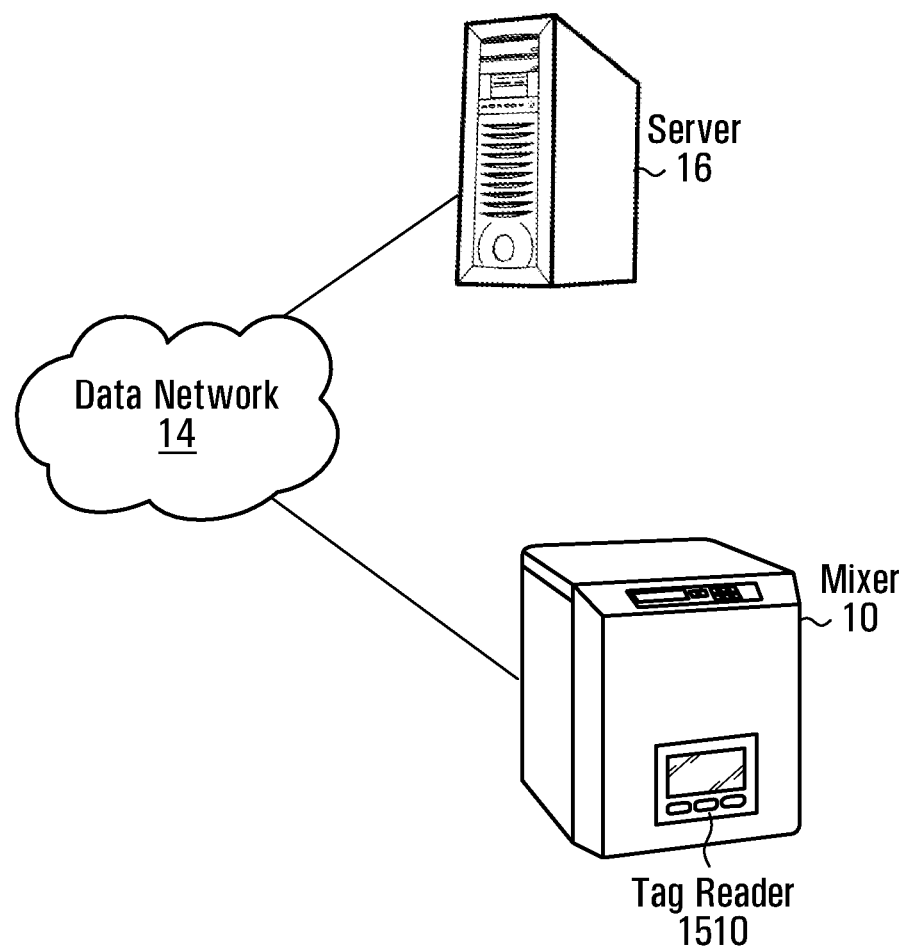

In a third embodiment, shown in FIG. 16C, the tag reader 1510 is built into the mixer 10, and the mixer 10 has a connection to the data network 14. In this case, the operating parameters are sent directly form server 16 to the mixer 10 over the data network 14.

In the latter two embodiments, the possibility of human error is significantly reduced as the user does not need to enter any data into the mixer 10. The tag-enabled container 1410 is simply read by the tag reader 1510, and the operating parameters for the desired formulation are sent to the mixer 10. As such, the individual performing the mixing phase does not need to be as skilled as the person performing the preparation phase. This could reduce operating costs and increase efficiency of a compounding pharmacy that implements the described method.

Figure 17:
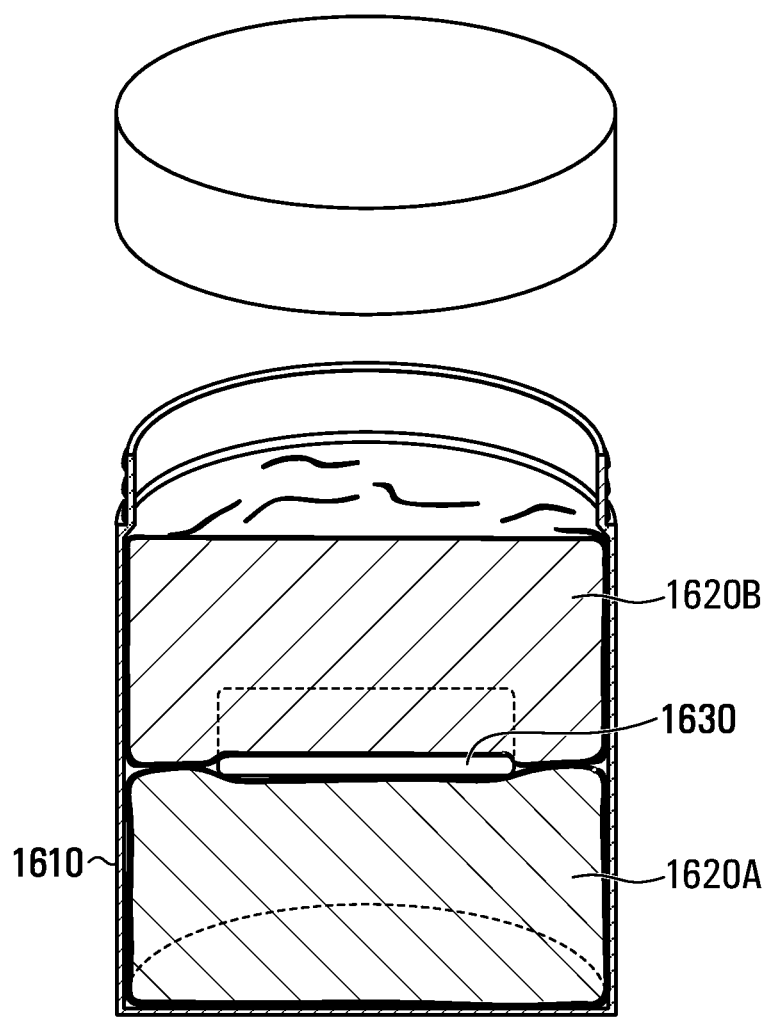
FIG. 17 shows an embodiment where a container to be mixed is fitted with a malleable adapter, in accordance with a non-limiting embodiment.

For the purposes of the following section, the container placed into the mixer 10 is referred to as a "mixing container". In an embodiment, and with reference to FIG. 17, the mixing container 1610 may be used with a universal adapter 1620, which allows the contents of a subject container 1630 placed inside the mixing container to be mixed. Typically, the mixing container 1610 may be a cylindrical jar, although this is not a limitation. As for the subject container 1630, its configuration is not particularly limited. It may be highly irregular. In some cases, the subject container 1630 may have a length dimension that exceeds the diameter or the height of the mixing container 1610 when the latter is a cylinder, such that it only fits when placed in diagonally.

The universal adapter 1620 fits inside the mixing container 1610 (e.g., cylindrical jar) and can be configured at least partly to espouse the shape of the inside of the subject container 1630, such as of the interior side and/or bottom walls of the subject container 1630. As shown in the non-limiting embodiment of FIG. 17, the universal adapter 1620 may have two (or more) parts, a first part 1620A that lies at the bottom of the mixing container 1610 and a second part 1620B that is added once the subject container 1630 has been placed onto the first part 1620A.

The first part 1620A and the second part 16206 may be made of the same material or of different materials. An example of a material that can be used for the first part 1620A and/or the second part 1620B can be a compressible foam. Certain desirable characteristics of the compressible foam include being able to espouse a contour of the subject container 1630 at rest while being sufficiently resistant to surface deformation at high rotation and revolution speeds. For example, the material can be designed or selected to as to be compressible at rest and yet to undergo no more than 1%, 3%, 5% or 10% surface deformation at 800 RPM rotation and 2000 RPM revolution. A non-limiting example of a commercially available compressible foam that may be suitable may include a polyurethane foam, a viscoelastic polymer foam, LDPE or EVA foam with a shore 00 hardness that ranges from about 20 to about 60.

A further example of a material that can be used for the first part 1620A and/or the second part 1620B can be a controllable-hardness material. One desirable characteristics of the controllable-hardness material includes the ability to be hardened prior to being subjected to high acceleration. In other cases, the material is chosen or designed to as to have an increased hardness by virtue of being subjected to acceleration; a non-limiting example of such a material is Polyborodimethylsiloxane, a non-newtonian fluid known commercially as D30 and described in U.S. Pat. No. 7,794,827. In some cases, application of an electrical current (e.g., charging) causes the material to acquire an increased hardness while charged. This allows the material to be molded while discharged and then to harden while charged, subsequent to which it is then subjected to planetary motion by the mixer 10. A non-limiting example of a controllable-hardness material that may be suitable may be based on the findings of Orolva et al., as described in the paper "Variation in Mechanical Properties Due to The Effect of Electric Potential", published as Dina Orlova et al 2017 *IOP Conf. Ser.: Mater. Sci. Eng.* 225 012218, hereby incorporated by reference herein.

In some embodiments, rather than being made of two parts, the universal adapter 1620 is made of a single part that has an opening for the subject container 1630.

In some embodiments, the universal adapter 1620 is made of a malleable material (e.g., putty), some of which can be compressed and moved out of the way to make room for the subject container and this removed material can be placed on top of the subject container 1630 to cocoon the subject container within the larger, mixing container 1610. In this case too, the universal adapter 1620 need not be made of two parts.

Due to its flexible, compressible and/or configurable nature, the universal adapter 1620 can be shaped so as to occupy a desired space within the mixing container 1610. As such, in some embodiments, the sum of the volume of the universal adapter 1620 and the subject container 1630 may occupy at least a certain threshold percentage of the total internal volume of the mixing container 1610 when empty. This threshold percentage may in some cases be 75%, in some cases more than 85%, in some cases more than 90%, in some cases more than 95% and in some cases more than 99% of the total internal volume of the mixing container 1610.

The use of a universal adapter 1620 allows the efficient mixing of different subject containers 1630 that have varying dimensions, without having to purchase an array of specialized adapters. This allows a compounding pharmacist to be efficiently handle different dosages and/or different manufacturers of subject containers, for example.

In an embodiment, and as previously described, planetary mixing may be used for particle size reduction, also referred to as milling or micronizing. In this case, and with reference to FIG. 18, there is provided a mixing container 1710 and milling beads 1720 (e.g., made of zirconium) may be placed into the mixing container 1710 together with the substance 1730 to be micronized. A cover 1740 may be placed onto the mixing container 1710, and the mixing container 1710 undergoes mixing by a planetary mixer, such as the mixer 10. Thereafter, the mixing container 1710 is removed from the planetary mixer, and the cover 1740 of the mixing container 1710 may be removed and replaced with a specialized filter cap 1800.

Figure 18:
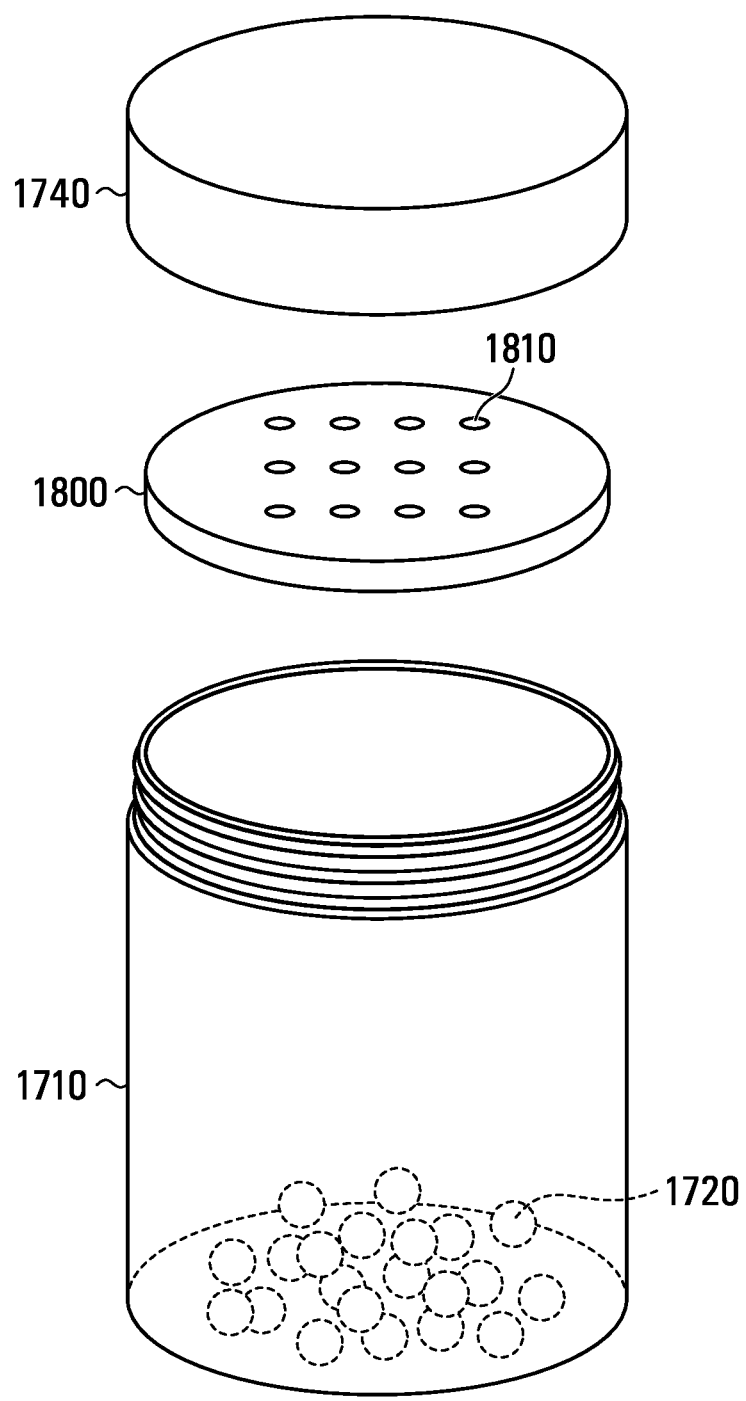
FIGS. 18, 19A and 19B show a container to which is fitted a filter head having a plurality of apertures, in accordance with a non-limiting embodiment.

As shown in FIG. 18, the filter cap 1800 is perforated, with holes 1810 that are smaller in dimension than the milling beads 1720. For example, if the beads 1720 are circular with a given diameter, the largest dimension of any of the holes 1810 is smaller than the aforementioned diameter. The filter cap 1800 serves to separate residual micronized powder (substance 1730 after particle size reduction) from the milling beads 1720, allowing the powder to escape the mixing container 1710 and the beads 1720 to remain. This reduces the loss of the substance (e.g., API) that was milled, resulting in less waste and, ultimately, greater savings for the compounding pharmacist.

Figure 19A:
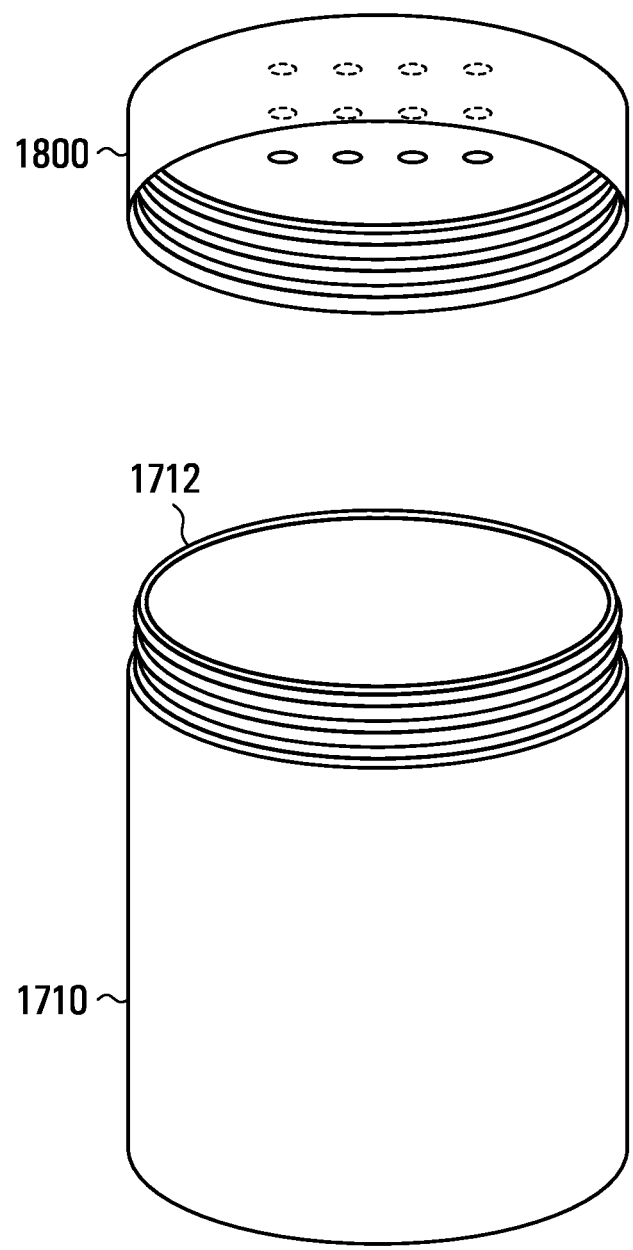
Figure 19B:
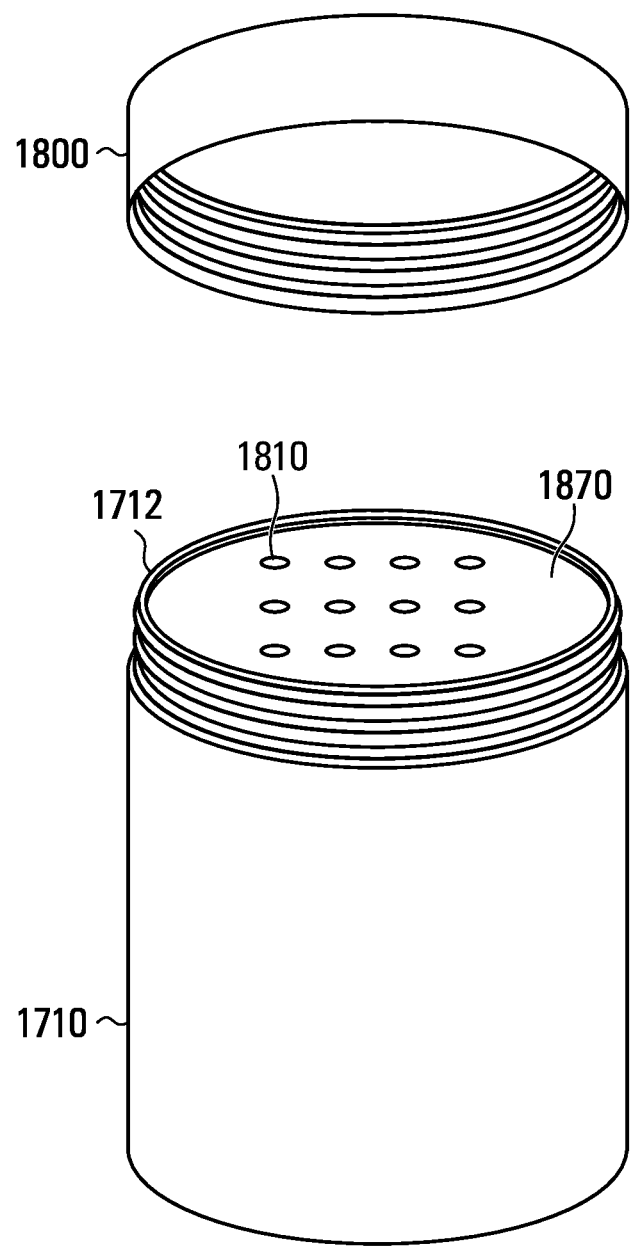

In one embodiment, shown in FIG. 19A, the filter cap 1800 is a replacement of the cover 1740, and can be screwed onto the mouth 1712 of the mixing container 1710 in lieu of the usual, exterior cover 1740. As such, the mouth 1712 and the cover 1740 have complementary threads, as do the mouth 1712 and the filter cap 1800. In another embodiment, shown in FIG. 19B, the filter cap is part of a two-piece cap with an exterior cap 1860 such that when the exterior cap 1860 is removed, the filter cap 1870 remains held in place underneath and secured to the mouth 1712 of the container 1710. For example, the filter cap 1870 may be press-fitted onto the mouth 1712 of the mixing container 1710. To remove the filter cap 1870, a tool may be used to reach behind the perforations 1810 and detach the filter cap 1870 from the mouth 1712 of the mixing container 1710.

Figure 22:
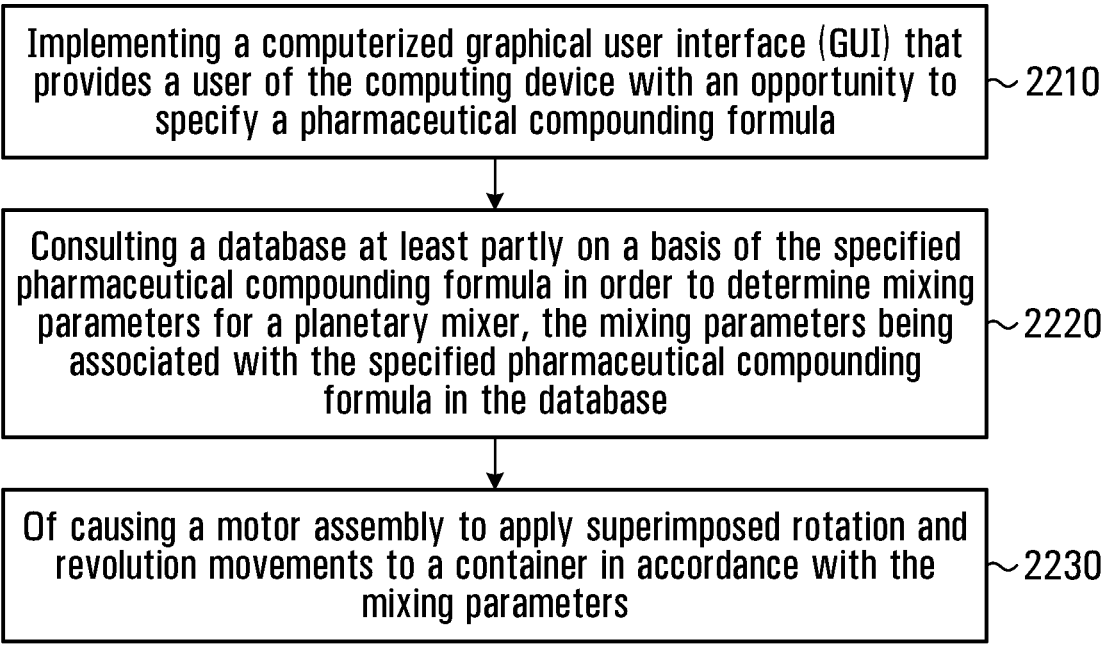
FIGS. 22 to 25 show various methods provided by various non-limiting embodiments.

As such, and with reference to FIG. 22, there has been provided a computer-implemented method for execution by a processor of a computing device, which comprises a step 2210 of implementing a computerized graphical user interface (GUI) that provides a user of the computing device with an opportunity to specify a pharmaceutical compounding formula. The method also comprises a step 2220 of consulting a database at least partly on a basis of the specified pharmaceutical compounding formula in order to determine mixing parameters for a planetary mixer, the mixing parameters being associated with the specified pharmaceutical compounding formula in the database. The method also comprises a step 2230 of causing a motor assembly to apply superimposed rotation and revolution movements to a container in accordance with the mixing parameters determined from step 2220.

Figure 23:
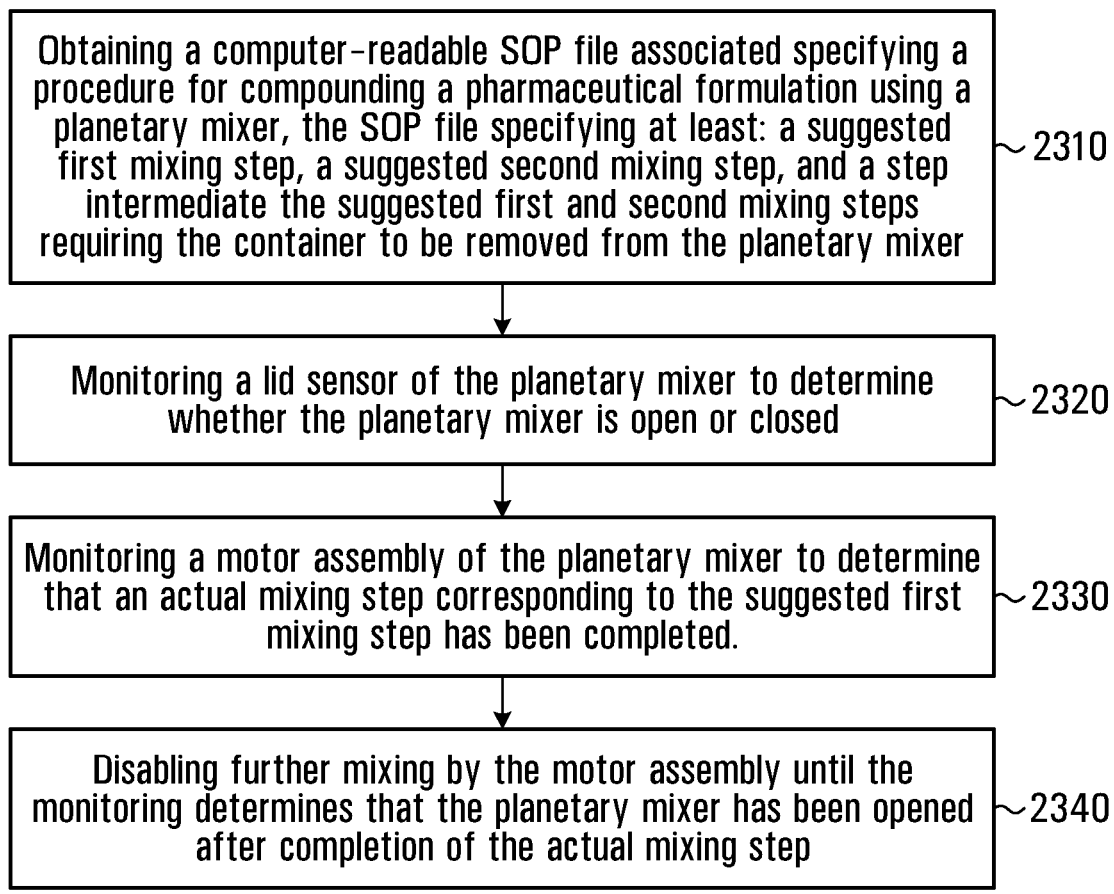

Also, and with reference to FIG. 23, there has been provided a computer-implemented method for compounding using a planetary mixer, which comprises a step 2310 of obtaining a computer-readable SOP file associated specifying a procedure for compounding a pharmaceutical formulation using a planetary mixer, the SOP file specifying at least: a suggested first mixing step, a suggested second mixing step, and a step intermediate the suggested first and second mixing steps requiring the container to be removed from the planetary mixer. The method also comprises a step 2320 of monitoring a lid sensor of the planetary mixer to determine whether the planetary mixer is open or closed. The method further comprises a step 2330 of monitoring a motor assembly of the planetary mixer to determine that an actual mixing step corresponding to the suggested first mixing step has been completed. Finally, the method comprises a step 2340 of disabling further mixing by the motor assembly until the monitoring determines that the planetary mixer has been opened after completion of the actual mixing step.

Figure 24:
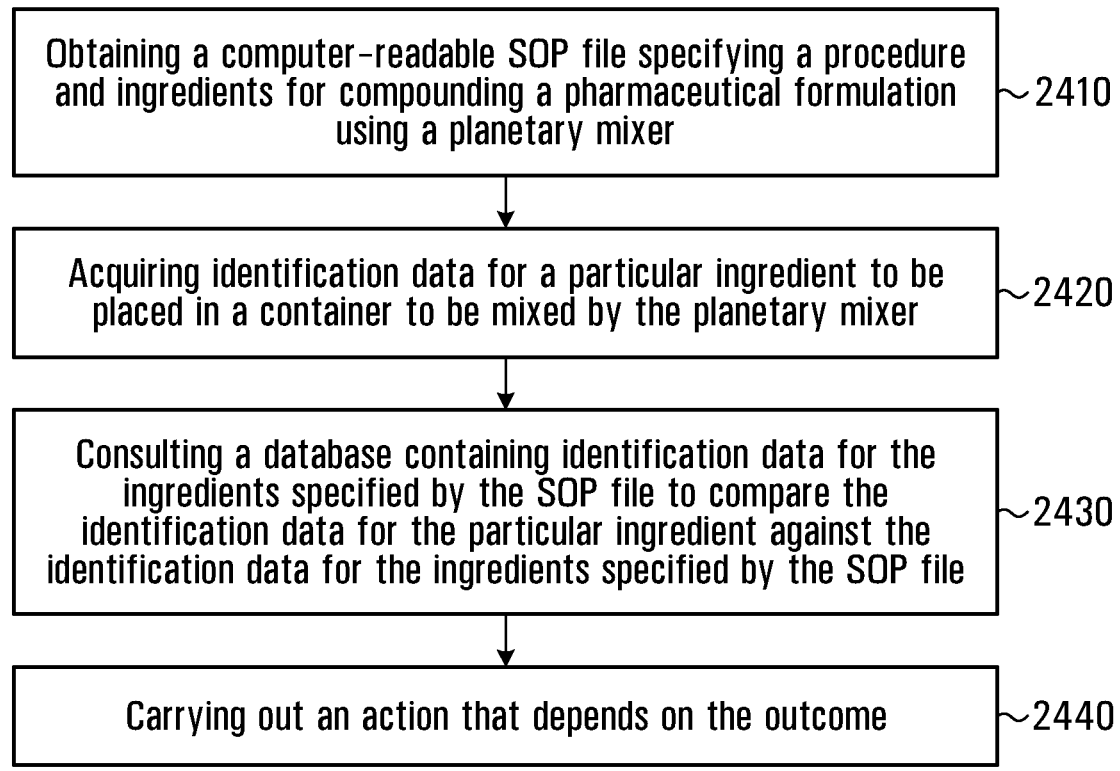

Also, and with reference to FIG. 24, there has been provided a computer-implemented method, which comprises a step 2410 of obtaining a computer-readable SOP file specifying a procedure and ingredients for compounding a pharmaceutical formulation using a planetary mixer. The method also comprises a step 2420 of acquiring identification data for a particular ingredient to be placed in a container to be mixed by the planetary mixer, as well as a step 2430 of consulting a database containing identification data for the ingredients specified by the SOP file to compare the identification data for the particular ingredient against the identification data for the ingredients specified by the SOP file. Finally, the method comprises a step 2440 of carrying out an action that depends on the outcome of step 2430.

Figure 25:
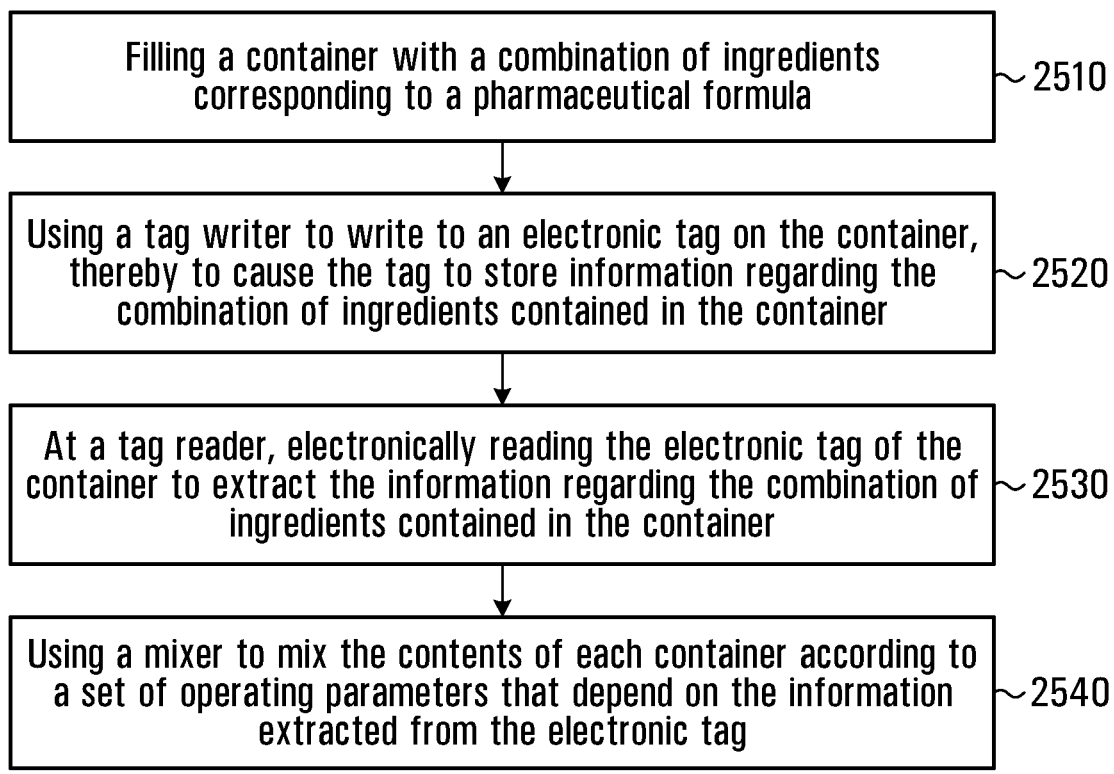

Also, and with reference to FIG. 25, there has been provided a manufacturing method, which comprises a step 2510 of filling a container with a combination of ingredients corresponding to a pharmaceutical formula; a step 2520 of using a tag writer to write to an electronic tag on the container, thereby to cause the tag to store information regarding the combination of ingredients contained in the container; a step 2530 of, at a tag reader, electronically reading the electronic tag of the container to extract the information regarding the combination of ingredients contained in the container; and a step 2540 of using a mixer to mix the contents of each container according to a set of operating parameters that depend on the information extracted from the electronic tag.

Of course, those skilled in the art will appreciate that the reference to tables throughout the disclosure is merely a conceptualization, as other organizational formats or data structures may be suitable and may thus be employed instead of tables.

Also, those skilled in the art will appreciate that further modifications can be made without departing from the scope of the invention, which is defined by the claims appended hereto.

What is claimed is:

1. A computer-implemented method for execution by a processor of a computing device, comprising:
   implementing a computerized graphical user interface (GUI) that provides a user of the computing device with an opportunity to specify a pharmaceutical compounding formula;
   consulting a database at least partly on a basis of the specified pharmaceutical compounding formula in order to determine mixing parameters for a planetary mixer, the mixing parameters being associated with the specified pharmaceutical compounding formula in the database;
   sending instructions to the planetary mixer to apply superimposed rotation and revolution movements, wherein the instructions convey at least one of a speed of the rotation movements and a speed of the revolution movements; and
   causing a motor assembly to apply the superimposed rotation and revolution movements to a container in accordance with the mixing parameters determined from the consulting step.

2. The computer-implemented method of claim 1, wherein the mixing parameters include the speed of the rotation movements, the speed of the revolution movements and a mixing time.

3. The computer-implemented method of claim 1, further comprising determining a weight of contents within the container.

4. The computer-implemented method of claim 3, wherein determining the weight of the contents of the container comprises receiving user entry of the weight via the GUI.

5. The computer-implemented method of claim 3, wherein determining the weight of the contents of the container comprises receiving a message from a weight scale configured to measure the weight of the contents of the container.

6. The computer-implemented method of claim 1, further comprising using a lid sensor to detect whether the mixer is open or closed and preventing the causing from being carried out if the mixer is determined to be open.

7. The computer-implemented method of claim 1, further comprising using a lid sensor to detect whether the mixer is open or closed and enabling the causing once the mixer is determined to be closed.

8. The computer-implemented method of claim 1, further comprising prompting the user of the computing device to select the specified pharmaceutical compounding formula from a menu of pharmaceutical compounding formulas presented via the GUI.

9. The computer-implemented method of claim 1, further comprising obtaining a weight of contents of the container and consulting the database on the basis of the specified pharmaceutical compounding formula and the weight, the database storing an association between sets of mixing parameters and respective combinations of pharmaceutical compounding formula and weight.

10. The computer-implemented method of claim 1, implemented by a mobile communication device, the method further comprising the mobile device sending messages to a planetary mixer comprising the motor assembly, the planetary mixer being remote from the mobile communication device, the messages comprising the mixing parameters.

11. A system, comprising:
a planetary mixer comprising a motor assembly configured to controllably apply superimposed rotation and revolution movements to a container;
a database storing pharmaceutical compounding formulas and associated mixing parameters indicative of at least one of a speed of a rotation movement and a speed of a revolution movement, and mixing duration; and
a communication device, comprising:
  a non-transitory storage medium storing computer-readable program instructions;
  at least one processor operably connected to the storage medium and configured to execute the program instructions, wherein execution of the program instructions by the at least one processor causes carrying out of a method that comprises:
    implementing a computerized graphical user interface (GUI) that provides a user of the communication device with an opportunity to specify a pharmaceutical compounding formula;
    consulting the database at least partly on a basis of the specified pharmaceutical compounding formula in order to determine mixing parameters associated therewith;
    sending instructions to the planetary mixer to apply the superimposed rotation and revolution movements, wherein the instructions convey at least one of a speed of the rotation movements and a speed of the revolution movements; and
    causing the motor assembly to apply the superimposed rotation and revolution movements to the container in accordance with the mixing parameters determined from said consulting.

12. A non-transitory medium storing computer-readable instructions which, when read and executed by at least one processor of a computing device, cause the device to carry out a method that comprises:
implementing a computerized graphical user interface (GUI) that provides a user of the computing device with an opportunity to specify a pharmaceutical compounding formula;
consulting a database at least partly on a basis of the specified pharmaceutical compounding formula in order to determine mixing parameters for a planetary mixer, the mixing parameters being associated with the specified pharmaceutical compounding formula in the database;
sending instructions to the planetary mixer to apply superimposed rotation and revolution movements, wherein the instructions convey at least one of a speed of the rotation movements and a speed of the revolution movements; and
causing a motor assembly to apply the superimposed rotation and revolution movements to a container in accordance with the mixing parameters determined from said consulting.

* * * * *